United States Patent
Anderson et al.

(10) Patent No.: US 12,070,303 B2
(45) Date of Patent: Aug. 27, 2024

(54) LOCATION AND ORIENTATION ESTIMATION OF DEVICES INCORPORATING PERMANENT MAGNETS

(71) Applicant: CloudNav Inc., San Jose, CA (US)

(72) Inventors: Erik E. Anderson, Menlo Park, CA (US); Jon D. Maiara, Malden, MA (US)

(73) Assignee: CloudNav Inc., San Jose, CA (US)

( * ) Notice: Subject to any disclaimer, the term of this patent is extended or adjusted under 35 U.S.C. 154(b) by 0 days.

(21) Appl. No.: 18/473,885

(22) Filed: Sep. 25, 2023

(65) Prior Publication Data

US 2024/0023823 A1 Jan. 25, 2024

Related U.S. Application Data

(62) Division of application No. 17/345,837, filed on Jun. 11, 2021, now Pat. No. 11,766,190.

(60) Provisional application No. 63/038,544, filed on Jun. 12, 2020.

(51) Int. Cl.
| | | |
|---|---|---|
| A61B 5/06 | (2006.01) | |
| A61B 5/287 | (2021.01) | |
| A61M 25/01 | (2006.01) | |
| G16H 20/40 | (2018.01) | |
| G16H 40/67 | (2018.01) | |
| A61M 25/09 | (2006.01) | |

(52) U.S. Cl.
CPC .......... *A61B 5/062* (2013.01); *A61M 25/0127* (2013.01); *G16H 40/67* (2018.01); *A61B 5/287* (2021.01); *A61B 2562/0223* (2013.01); *A61M 25/09* (2013.01); *G16H 20/40* (2018.01)

(58) Field of Classification Search
CPC . A61B 5/062; A61B 5/287; A61B 2562/0223; G16H 40/67; G16H 20/40; A61M 25/0127; A61M 25/09
See application file for complete search history.

(56) References Cited

U.S. PATENT DOCUMENTS

| | | |
|---|---|---|
| 6,263,230 B1 | 7/2001 | Haynor et al. |
| 2007/0135803 A1 | 6/2007 | Belson |
| 2010/0121188 A1 | 5/2010 | Sandhu et al. |
| 2011/0092761 A1 | 4/2011 | Almog et al. |
| 2014/0031674 A1 | 1/2014 | Newman et al. |
| 2019/0175266 A1 | 6/2019 | Wu et al. |

*Primary Examiner* — John D Li

(74) *Attorney, Agent, or Firm* — Perkins Coie LLP

(57) ABSTRACT

Methods, systems and devices for estimating the position and orientation of an invasive surgical devices, for example, a catheter guidewire or endoscope, surgical catheter, or self-guided electrophysiology catheter, relative to a reference frame, are described. An example system comprises one or more permanent magnets mounted on the surgical device, a plurality of magnetometer sensors at fixed location providing a reference frame that are configured to perform magnetic field measurements of the direct current superposition field of the permanent magnets, and computational means for receiving the input signals and calculating the position and orientation of the permanent magnets mounted on the surgical device.

20 Claims, 34 Drawing Sheets

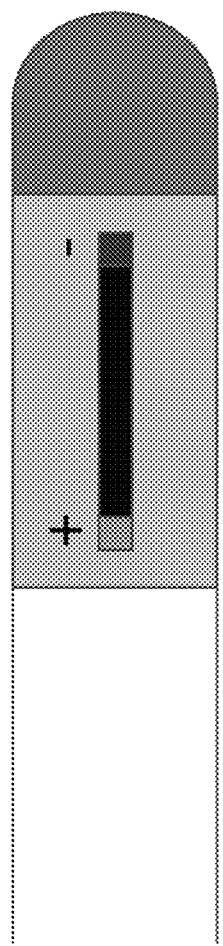
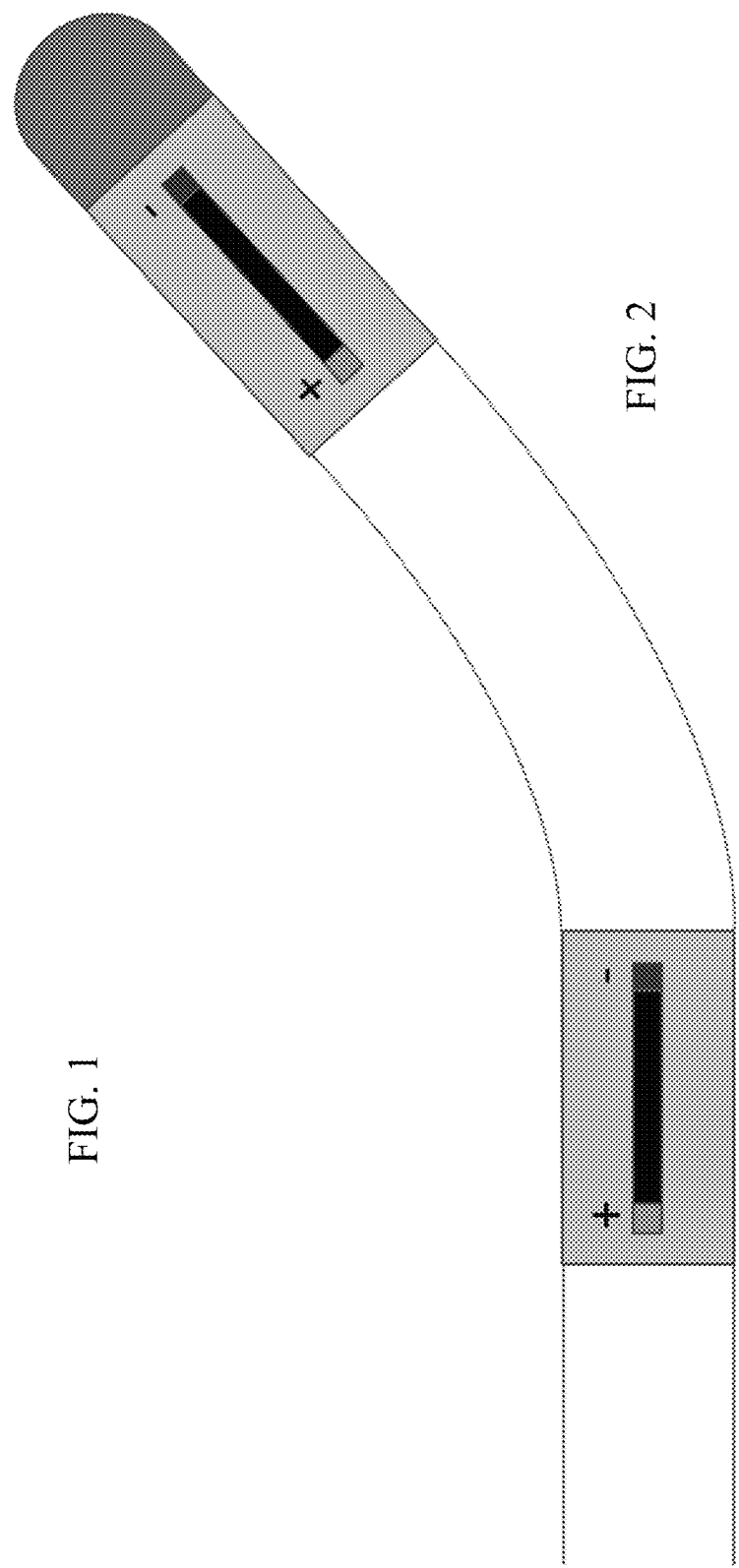
FIG. 1
FIG. 2

LOCATION AND ORIENTATION ESTIMATION OF DEVICES INCORPORATING PERMANENT MAGNETS

CROSS-REFERENCE TO RELATED APPLICATION

This patent document is a divisional of U.S. Non-Provisional patent application Ser. No. 17/345,837, filed on Jun. 11, 2021, which claims priority to and benefits of U.S. Provisional Patent Application No. 63/038,544, filed on 12 Jun. 2020. The entire content of these patent applications are incorporated by reference as part of the disclosure of this patent document.

TECHNICAL FIELD

This document generally relates to localization, and more particularly to estimating the location and orientation of devices incorporating permanent magnets.

BACKGROUND

During both diagnostic and therapeutic procedures, it is often necessary or desirable to determine the location of a medical probe. For example, a catheter or catheter guidewire must typically be navigated through a patient's body in order to locate the operative portion of the catheter adjacent to a target tissue region. Traditionally, this has been accomplished using fluoroscopy, a time series of X-ray bursts each of which can provide partial position information at a snapshot in time of the surgical device and the body. However, there are significant limitations and undesired properties of fluoroscopy.

SUMMARY

Embodiments of the disclosed technology relates to methods, systems and devices for estimating the location and orientation of devices incorporating permanent magnets. The methods and devices described in the present document advantageously, among other features and benefits, allow the physician and medical team unrestricted access to the patient with no physical blockages due to the localization system, and provide accurate position and orientation information at a consistently high data rate for real-time visualization.

In an example aspect, a system for estimating a location or an orientation of an invasive medical device includes one or more permanent magnets incorporated into the invasive medical device, a plurality of magnetic field sensors arranged in a specific topology separate from the invasive medical device, the plurality of magnetic field sensors configured to obtain a plurality of magnetic field measurements of the one or more permanent magnets of the invasive medical device, and one or more processors, coupled to the plurality of magnetic field sensors, configured to receive the plurality of magnetic field measurements, and enable a calculation of the location or the orientation of the one or more permanent magnets based on the plurality of magnetic field measurements.

In another example aspect, a method for obtaining a location or an orientation of an invasive medical device inside a patient includes receiving, from a plurality of magnetic field sensors arranged in a specific topology separate from the invasive medical device, a first plurality of magnetic field measurements associated with one or more permanent magnets incorporated into the invasive medical device that is at a first position within the patient, determining the location or the orientation of the invasive medical device at the first position based on the first plurality of magnetic field measurements, receiving, from the plurality of magnetic field sensors, a second plurality of magnetic field measurements associated with the one or more permanent magnets, wherein the invasive medical device is at a second position within the patient, and updating the location or the orientation of the invasive medical device by determining the location or the orientation of the invasive medical device at the second position based on the second plurality of magnetic field measurements.

In yet another example aspect, the above-described methods may be implemented by an apparatus or device that comprises a processor and/or memory.

In yet another example aspect, these methods may be embodied in the form of processor-executable instructions and stored on a computer-readable program medium.

The subject matter described in this patent document can be implemented in specific ways that provide one or more of the following features.

BRIEF DESCRIPTION OF THE DRAWINGS

FIG. 1 illustrates an example of a catheter with a permanent magnet near the distal tip with an active electrophysiology (EP) end-cap.

FIG. 2 illustrates an example of a catheter with two permanent magnets, and with an active EP end-cap.

DETAILED DESCRIPTION

Figure 3:
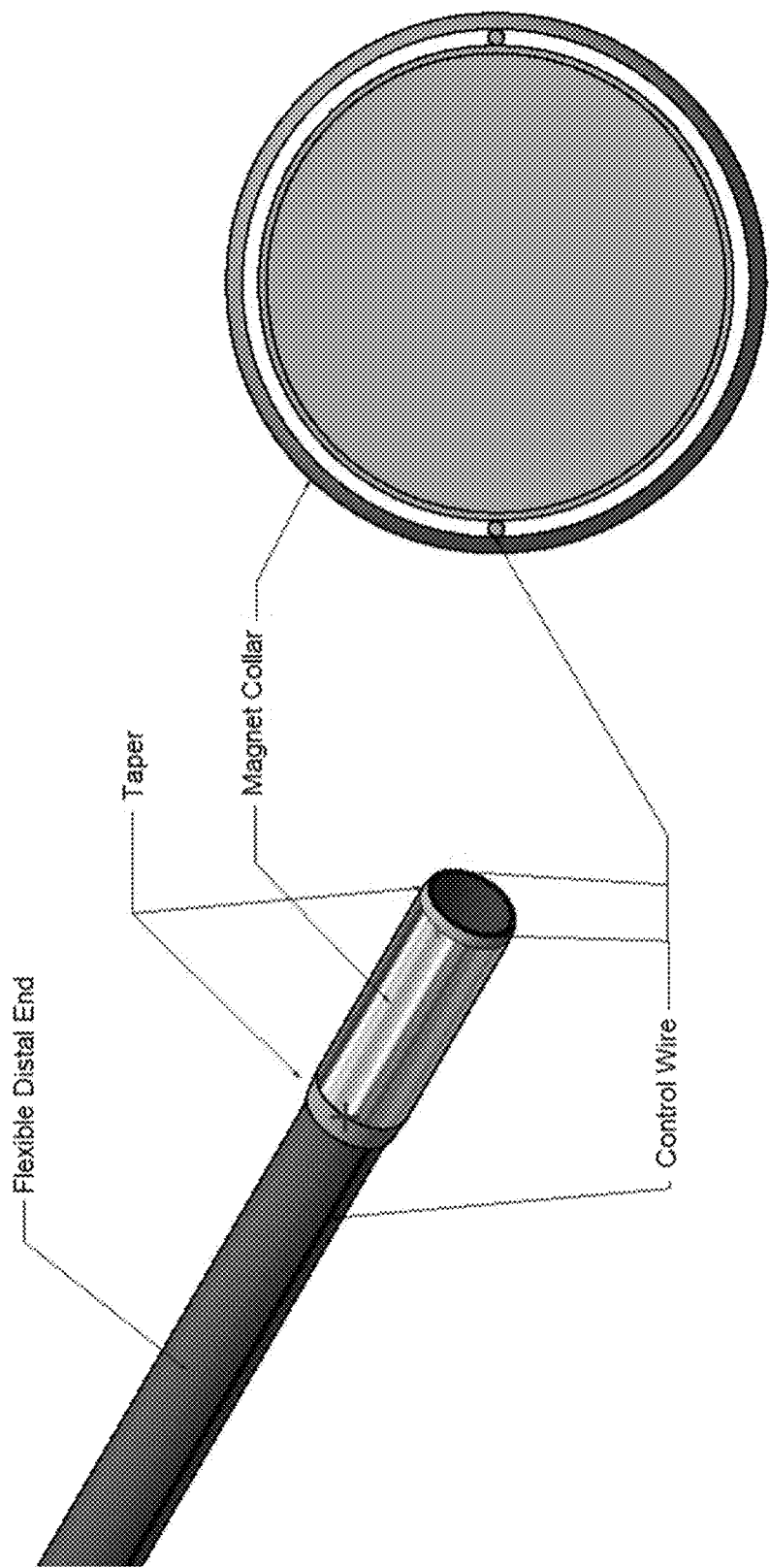
FIG. 3 illustrates an example of a catheter guidewire with a cylindrical magnet surrounding one or more central lumens.

Existing systems for in-body localization use fluoroscopy, which uses a time series of X-ray bursts each of which can provide partial position information at a snapshot in time of the surgical device and the body. In this case, radiopaque elements are located on the distal end of the catheter and repeated X-ray projections are taken to continuously update the image as the catheter is routed through the body. The result is a two-dimensional image of the catheter which allows the physician to roughly determine the location of the catheter. There are significant limitations and undesired properties of fluoroscopy.

(1) Fluoroscopic output gives an incomplete view of position and orientation of the device within the body, as it provides only a two-dimensional projection. A more complete imaging technique should provide 3D position and orientation.

(2) Fluoroscopy during diagnostic and therapeutic procedures inherently exposes the patient to unwanted and harmful ionizing radiation. There is also a corresponding unwanted radiation dose to the surgeon and surgical team. As a result, both the patient and the medical team need to be heavily shielded, which invariably interferes with the latter's movements during medical procedures. Fluoroscopic X-ray measurements are repeated typically over a repeated measurement rate of about 4 Hz to 20 Hz, to provide real-time visualization for the physician, resulting in substantial total radiation dose throughout the procedure. At the higher repeat rate (20 Hz), radiation dose is greatly increased, while at the lower repeat rate (4 Hz), the output image can appear to both lag in time and jump in space during periods of significant motion.

Some methods have been developed which improve localization of radiation compared to the conventional fluoroscopic system. These methods include electromagnetic systems, optical systems, magnetic systems, and acoustic systems. Existing systems which use magnetic localization techniques include:

(1) Electromagnetic field generator beacons in a fixed reference frame are combined with one or more medical-device mounted magnetometer sensors. In these systems, drive signals are applied to the electromagnetic beacons which send out time-varying magnetic signals. These are typically continuous alternating current (AC) signals where each magnetic beacon broadcasts at its own frequency to make the signal from each beacon distinguishable from all other beacons while all beacons are driven simultaneously. Sensors means for measuring magnetic field are mounted on the medical device, and there are computational means for calculating individual field strength and direction for a given generated field at each frequency, analysis of phase-differences and cross-correlation between the inputs.

In some embodiments, a magnetometer sensor includes a small-scale micro-electromechanical system (MEMS) device for detecting and measuring magnetic fields, which operates by detecting effects of the Lorentz force—a change in voltage or resonant frequency may be measured electronically, or a mechanical displacement may be measured optically.

(2) Sequentially-applied magnetic gradient fields. These systems typically use 3 large coil-pairs surrounding the patient aligned orthogonally. The coils are sequentially driven in pairs to produce a gradient field normal to the coil-pair axis, such that the spatial position varies linearly with the value of the magnetic gradient field in that direction. An estimate for one directional component of position can be directly measured during each coil-pair drive cycle.

(3) An electrical system that works analogously to the sequentially-applied magnetic gradient field. This system performs localization by observing a voltage gradient. Signals are sequentially applied across electrode pairs to generate AC electric fields sequentially on 3 different axes. Electrodes are mounted on the in-body medical device which measure the voltage compared with an externally applied reference voltage. When the generator applies voltage on a particular axis, the spatial information is encoded within the resulting voltage along the generated electric field.

(4) Systems where electromagnetic signals are propagated between one antenna on the tip of a medical catheter inserted in the body and several antennas outside the body. The position and orientation of the catheter tip are determined from the signals transmitted between these antennas.

Existing systems for magnetic in-body localization use electromagnets with controllable drive circuitry in order to enable and disable the magnetic field sequentially by axis, and to control the generated field frequency in order to differentiate each individual radiator. This makes the problem of localization computation easier in many ways, but also pushes significant complexity and operating constraints onto other parts of the system.

Embodiments of the disclosed technology, among other features and benefits, overcome at least the following limitations of current systems:

(1) External radiators often interfere with accessibility to the patient.
  (a) This is the case with coil pairs to produce magnetic gradient fields. These systems are large and expensive, typically completely surround the patient, and require a dedicated surgical suite to be built around the system.
  (b) Systems with magnetic beacons are mounted with some beacons at or below the level of the patient and one or more elements above the patient, which restricts the ability of the physician to freely access the patient.

(2) A small form factor for the device-mounted localization system components is critical. Any increase in the size of the invasive medical device reduces the physician's options regarding where within the body the device may be positioned. This is a significant problem whether the device contains a magnetic beacon or magnetic field sensors. In the case of device-mounted magnetic beacons, the drive coils must be precisely mounted within the invasive device, for example, at the distal tip of a catheter guidewire. In the internal beacon case, the applied signal and sufficient drive current must be routed to the in-body radiator. This can be achieved with additional wires to carry signal with significant current or implemented with on-board drive circuitry and a radio-link. In either case, there is a significant problem to be overcome in implementing the beacon system in a space-constrained way. The more common system choice is to have 3D magnetometer sensors integrated within the invasive medical device, typically with separate receive coils arranged along 3 orthogonal axes. Associated with the receive coils are on-board low noise amplifiers and signal wires between the internal device and the rest of the system outside the body. The issue is compounded if the system intends to locate more than one reference point along the medical device. For a transmitting beacon, a separate drive system and radiators must be embedded within the device for each reference location. Alternatively, a separate set of sensing coils or other magnetic field sensing devices must be integrated for each internal device reference point.

(3) There is an additional problem with both radiating or receiving coil-sets on the internal medical device, which is also related to the size of the transmitters and/or receivers at the reference points. The x, y, and z coils are not zero size. This means that each of the single dimension coils and/or field sensors is at a slightly different position within the device than the intended reference position. Also, for best maneuverability, it is highly desirable that the in-body device be flexible, which can add an error to the relative orientation of the coils making them no longer orthogonal.

(4) The best of these systems currently achieves positional accuracy of 1-2 mm.

Embodiments of the disclosed technology provide, amongst other features and benefits, the following:

(1) Small footprint on-board the internal medical device;
(2) Allowing the physician and medical team unrestricted access to the patient with no physical blockages due to the localization system;
(3) Complete three-dimensional position and orientation information of the device in the body;
(4) Elimination (or at least a significant reduction) of the inherently harmful dose of ionizing radiation received by the patient and surgical team during medical procedures; and
(5) Accurate position and orientation information (much better than current state of the art 1 mm accuracy) at a consistently high data rate for real-time visualization.

According to some embodiments, one or more reference positions on a medical device are localized, providing an estimate of both position and orientation. The device may be flexible, such that the orientations of different reference points on the device may be different. The disclosed systems do not require radiating coils requiring drive current, receive coils or other magnetic field sensing devices, but the localization system can include one or more permanent magnets integrated within the medical device. This system does not require any device-mounted drive circuitry, control logic, or additional wires to achieve localization of the medical device.

According to some embodiments, an array of magnetometer sensors measures 3D magnetic field information at a plurality of reference locations outside of the in-body device. This sensor array defines a positional reference frame for the magnetic location system. In some embodiments, the sensor array is planar, located below the patient, and can be integrated with or attached to the operating table. In a planar configuration below the patient, the sensor array achieves the goal of zero obstruction of physician access to the patient. The receive sensor array may also be non-planar, so long as the sensor locations are known.

In some embodiments, the sensor array can be configured as a regular planar grid with each sensor performing 3 orthogonal magnetic field measurements. In other embodiments, many other geometries can be implemented. For example, the set of sensors can be planar but with irregular separations between the sense elements. The sense elements can also be mounted arbitrarily in three dimensions, so long as positions of the sensor elements are known. For arbitrary sensor locations in x, y and z axes, the orientation of each sensor can also be arbitrary, as the fields from each sensor can be rotated via an individual mounting matrix for each 3D sensor into a common sensor reference frame. Furthermore, the sensors do not need to include 3 orthogonal measurements taken at the same location. For example, magnetometer sensors making a single field measurement along an axis can be used for the sensor array, as long as projections of the individual measurement axes onto the coordinate axes of the common sensor reference frame overlap sufficiently.

Embodiments of the disclosed technology exhibit improved performance when the permanent magnets of the surgical device lie approximately within the x-y bounds defined by the outer sensors in the sensor grid, and when the height above the grid is less than or equal to twice the x-y grid width. Measured accuracy error increases as the permanent magnets are moved outside of this guideline work volume. However, there is a graceful degradation in performance as the magnets move outside the aforementioned work volume.

Electrophysiology (EP) catheters are specialized catheters, which are designed to be used with compatible stimulators and/or amplifiers to perform standard electrophysiology studies. Depending on the features of the stimulator/amplifier, pacing and recording protocols can be performed from inside the heart (intracardiac) or through the esophagus (transesophageal) to determine electrical properties of the atrium and the ventricle, which include:

Conduction times
Refractory periods
His potentials
Sinus and atrioventricular nodal properties
Inducibility of abnormal heartbeats Embodiments of the disclosed technology enable the localization of EP catheters based on the catheters being configured with one or more permanent magnets. FIGS. 1 and 2 show examples of EP catheters with one and two magnets, respectively. As illustrated therein, the catheters can be configured to include one or two permanent magnetic dipoles (e.g., a bar magnet with positive and negative poles separated by a distance). FIG. 3 shows an example of a catheter guidewire with a cylindrical magnet surrounding one or more central lumens.

Examples of Medical Devices Incorporating One or More Permanent Magnets

In some embodiments, using a single catheter guidewire-mounted permanent magnet and a planar array of 3D magnetometer sensors results in an accuracy in locating the catheter position of <0.3 mm. In other embodiments, using two permanent magnets on a flexible catheter guidewire results in a simultaneous accuracy for both permanent magnets of <0.3 mm. In both of these example embodiments, reference locations are updated without noticeable delay, at, for example, a 50 Hz rate.

Figure 4A:
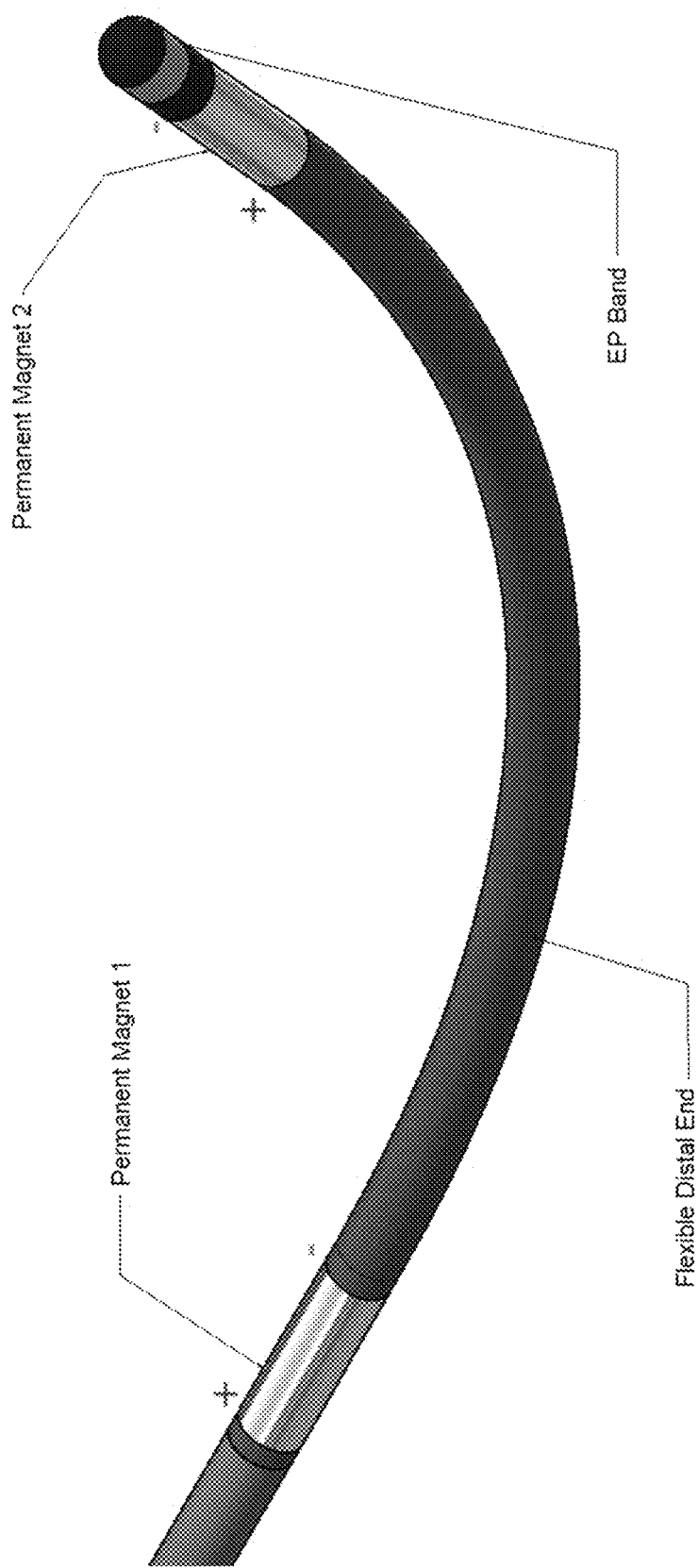
FIG. 4A illustrates an example of a catheter guidewire with two cylindrical magnets, surrounding one or more central lumens, separated by a flexible wire section.

In the multiple (two or more) magnet embodiments, the section of catheter guidewire between the two magnets can be flexible (as illustrated in FIG. 4A), so that each magnet along the wire may have a unique angular orientation.

In some embodiments, the wire rotational compliance is a function of position along the wire. In this case, the radius of curvature at each point is inversely proportional to the distributed compliance value at that point. Alternatively, the radius of curvature is proportional to the distributed rotational stiffness (1/rotational compliance) at each point along the wire. The rate of change of deflection at each point is proportional to the compliance multiplied by the bending moment.

Figure 4B:
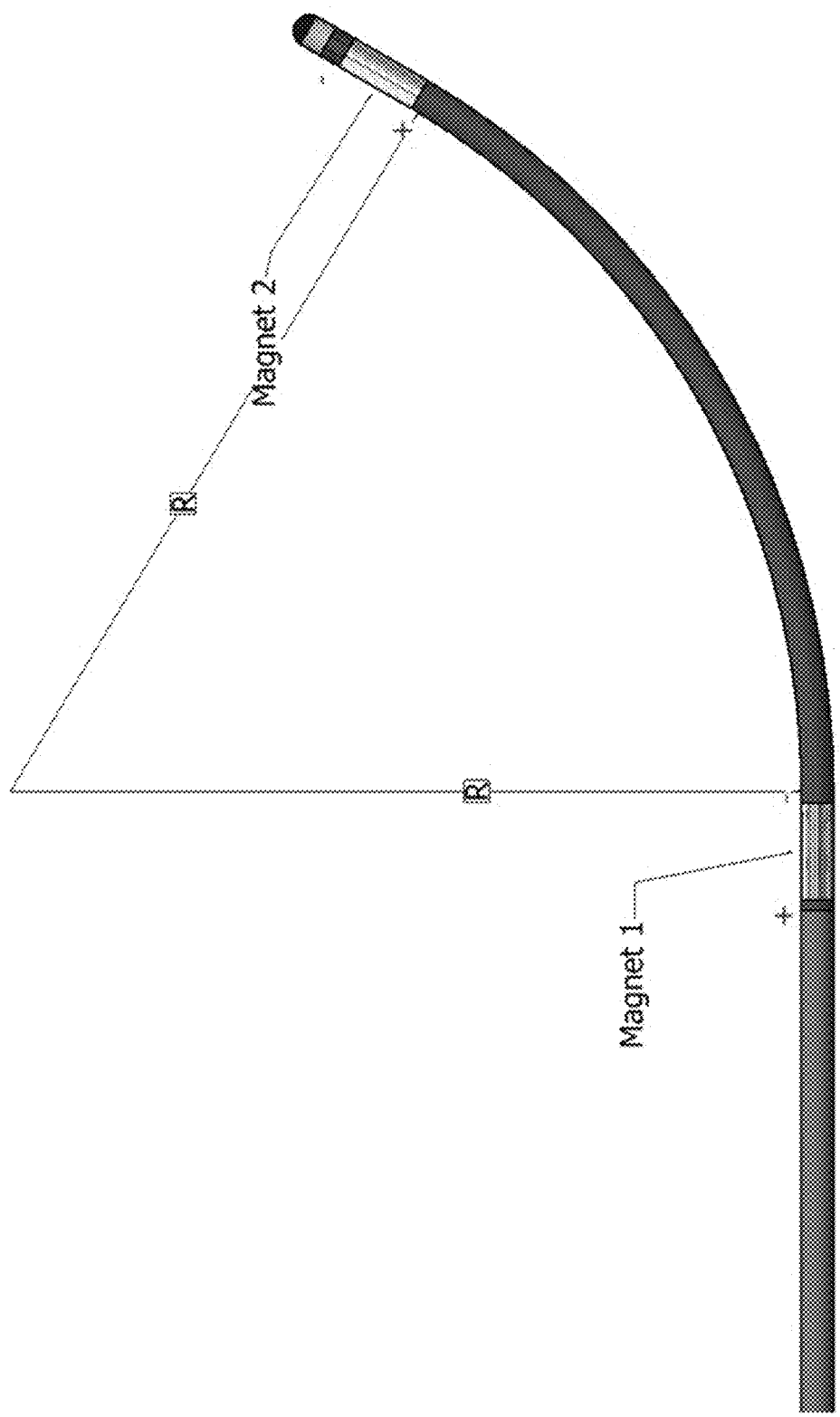
FIG. 4B illustrates another example of a catheter guidewire with two cylindrical magnets, surrounding one or more central lumens, separated by a flexible wire section with a constant radius of curvature.

In some embodiments, the distributed compliance along the flexible section of the wire is constant throughout the flexible section bounded by the proximal and distal magnets. In this case, the shape of the flexible wire segment between the permanent magnets is a circular arc (as illustrated in FIG. 4B).

Figure 5:
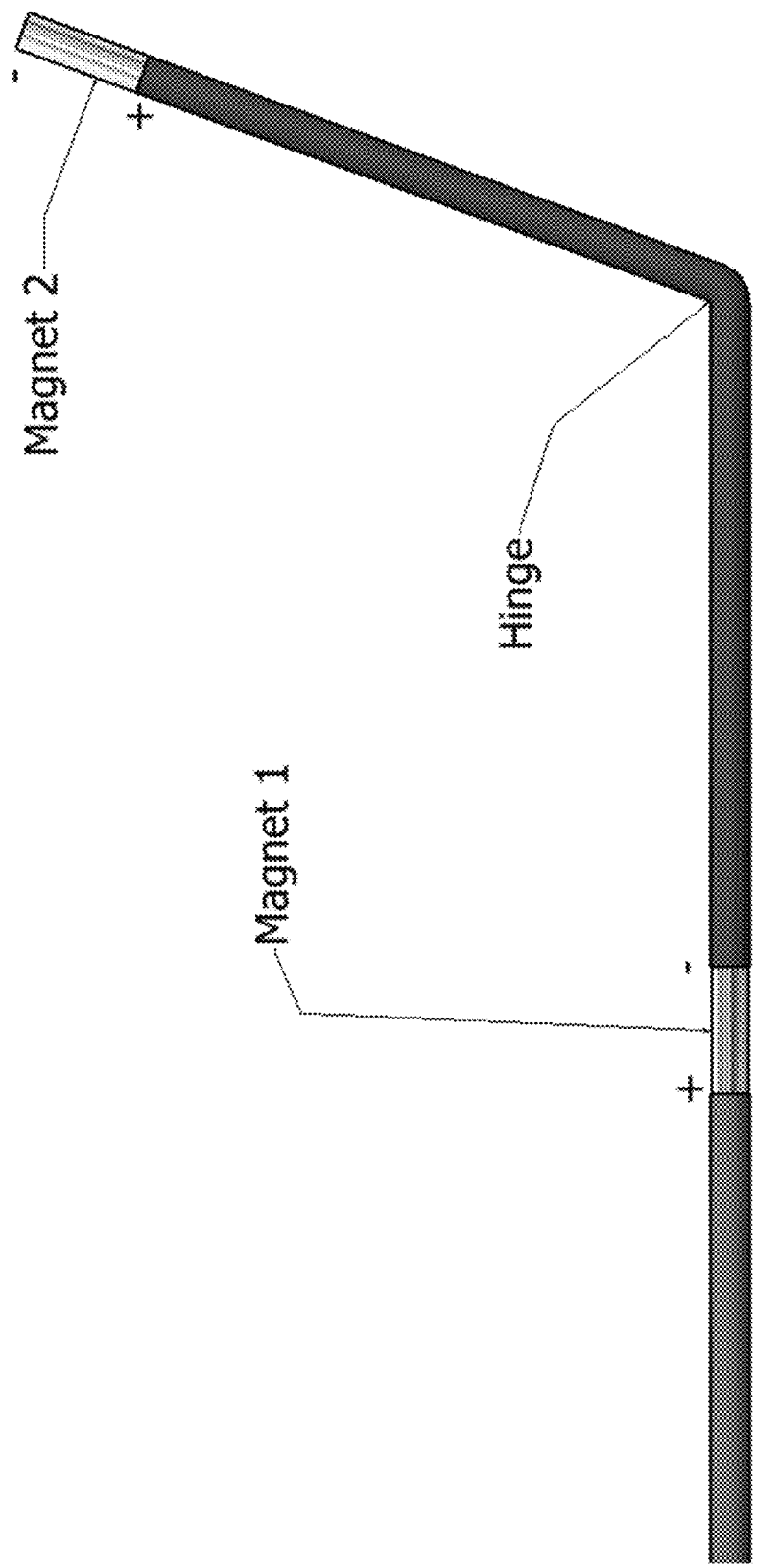
FIG. 5 illustrates an example of a catheter guidewire with two cylindrical magnets, surrounding one or more central lumens, separated by a hinge-section.

In some embodiments, the catheter guidewire flex is implemented as a single hinge-point with rigid sections proximal and distal to the hinge, with the two magnets on either side of the hinge (as illustrated in FIG. 5).

According to some embodiments, in the two-magnet configurations (e.g., the examples illustrated in FIGS. 4A, 4B and 5), the positions and orientations of the magnets can be accurately described with 7 parameters: x, y, and z for first magnet center, theta (θ, azimuth of first magnet, corresponding to rotation around the x-plane), phi (φ, elevation of first magnet), a deflection parameter α, and a rotation angle eta (η) of the two magnet system about the first magnet axis. With the correct value of the deflection parameter α, and a model of the distributed mechanical compliance along the wire, the complete curve of the flexible wire section between the two magnets can be correctly modeled.

Example embodiments that are described using the 7-parameter model use the following set of parameters: x, y, and z for Magnet 1 (M1) position, theta (yaw-angle) corresponding to rotation about the reference frame z-axis (wherein a 0 value for yaw means x-y plane projection of magnetic axis is along the x-axis), phi (elevation, wherein a 0 elevation corresponds to magnet axis in the x-y plane and a pi/2 radian elevation corresponds to magnet axis along z-axis), eta rotation about the M1 axis, and the deflection parameter a.

In the example of the two-magnet hinge embodiment (illustrated in FIG. 5), the deflection parameter α is simply the angle made by the hinge.

Figure 6:
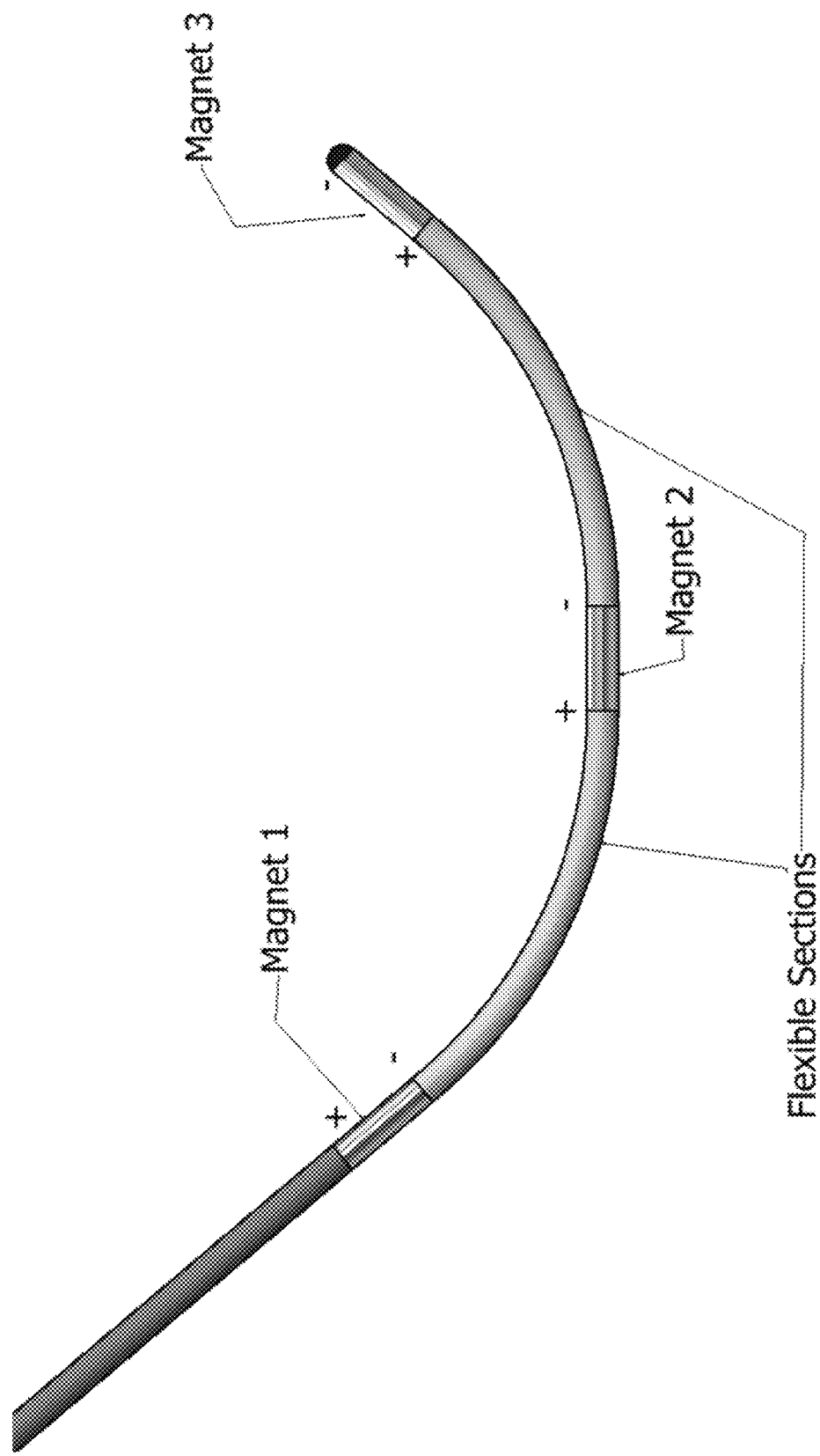
FIG. 6 illustrates an example of a catheter guidewire with three cylindrical magnets, surrounding one or more central lumens, separated by flexible wire sections.

In some embodiments, more than two magnets can be incorporated along the flexible section (as illustrated in FIG. 6). As in the two-magnet case, the wire has a distributed compliance as a function of distance along the flexible section and the shape of the flexible section is determined by the bending moment and the distributed wire mechanical compliance. The path lengths along the wire between each magnet are known so that the relative magnet positions can be calculated given the flexible section wire shape resulting from the bending moment and the flexible wire distributed mechanical compliance. This method can be extended to any number of fixed magnets.

In some embodiments, the distributed wire compliance model may be a simplification of the true wire distributed compliance, such that the best fit deflection parameter α does not yield an exact solution of the flexible wire shape. In this case, the calculated permanent magnet positions and orientation will also not be exact. Herein, precise positions and orientation of each magnet will require an additional optimization stage. Using an exact model includes two stages: a first stage that uses geometric feature extraction to determine approximate parameters, which are input into the second stage that implements an optimization of the 7-parameter model.

However, when the combination of distributed mechanical compliance and best fit deflection parameter are not exact, a three-stage approach can be used. The first two stages are the same as described above, and then the third stage includes passing the approximate 7-parameter estimate to a more general 5×N dimensional optimizer, where N is the number of magnets. In this optimizer, each magnet's x, y, and z positions, as well as azimuth and elevation parameters, are independent. Given the 7-parameter model, the x, y, and z coordinates for the positive and negative poles of each magnet can be calculated. Each pair of poles (for each cylindrically symmetric dipole magnet) can then be described with the 5-parameter model used for the single magnet system, with the x, y, z, theta and phi parameters being relative to the sensor reference frame. Thus, for a two-magnet system, this is a 10-dimensional optimizer, for a 3 magnet system this is a 15-dimensional optimizer, and so on. In order for the optimizer to reach the correct answer, the closest minimum for the 5×N-dimensional error function must also be the global minimum. The intermediate 7D optimizer is configured to find a set of parameters close enough to the global minimum so that the 5×N dimensional error optimization will converge.

In some embodiments, one or more permanent magnets are mounted on the catheter guidewire as hollow cylindrical collars leaving the guidewire lumens unobstructed. In other embodiments, the one or more permanent magnets are mounted along the geometric axis of the guidewire near the distal tip, which blocks the central lumen at that point. This configuration can be used with catheters that travel on the outside of the guidewire, such as a balloon catheter.

Figure 7:
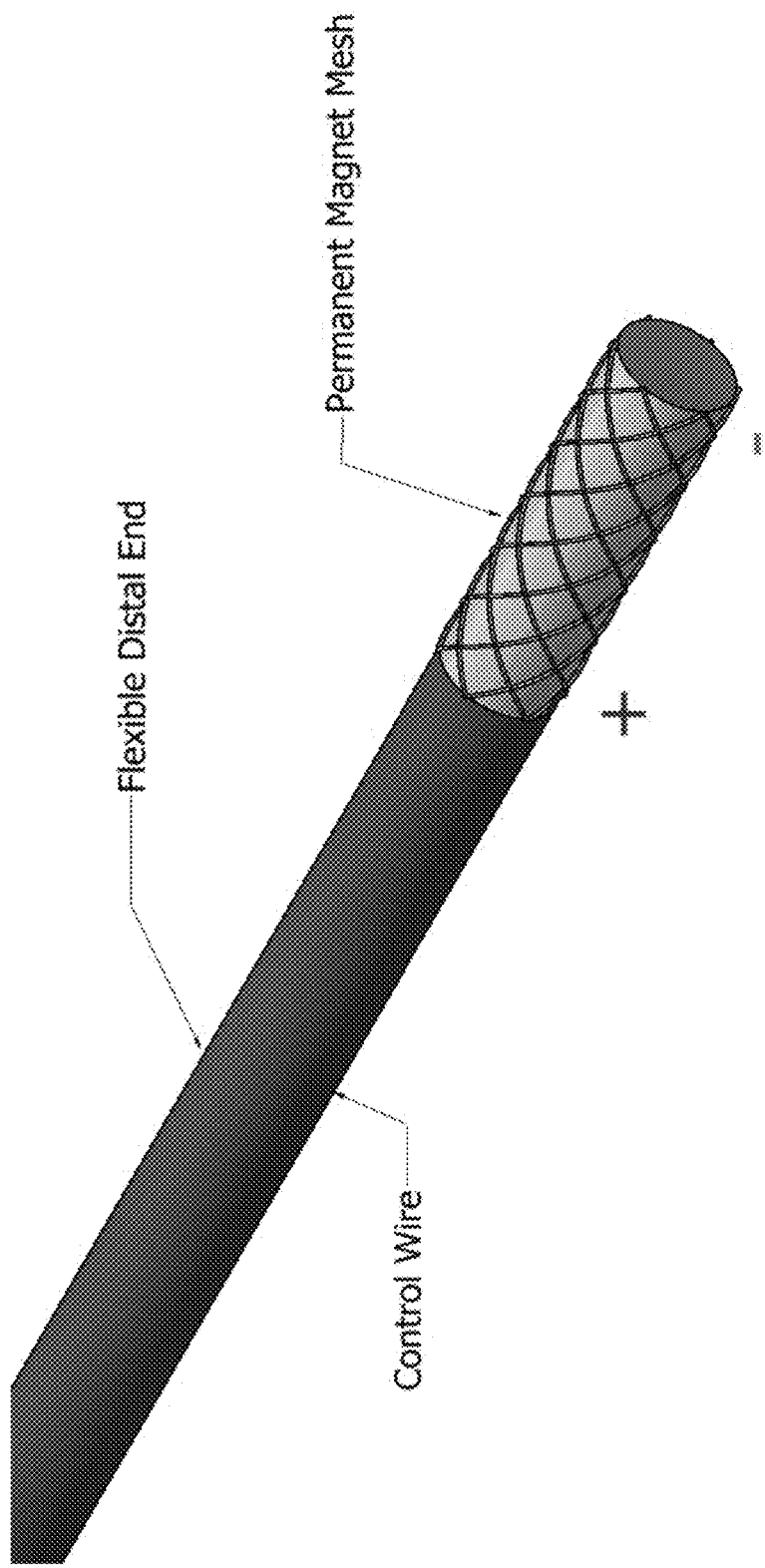
FIG. 7 illustrates an example of a catheter guidewire wherein part of the guidewire near the distal tip has been permanently magnetized, and is constructed from stainless steel mesh integrated within the catheter.
Figure 8:
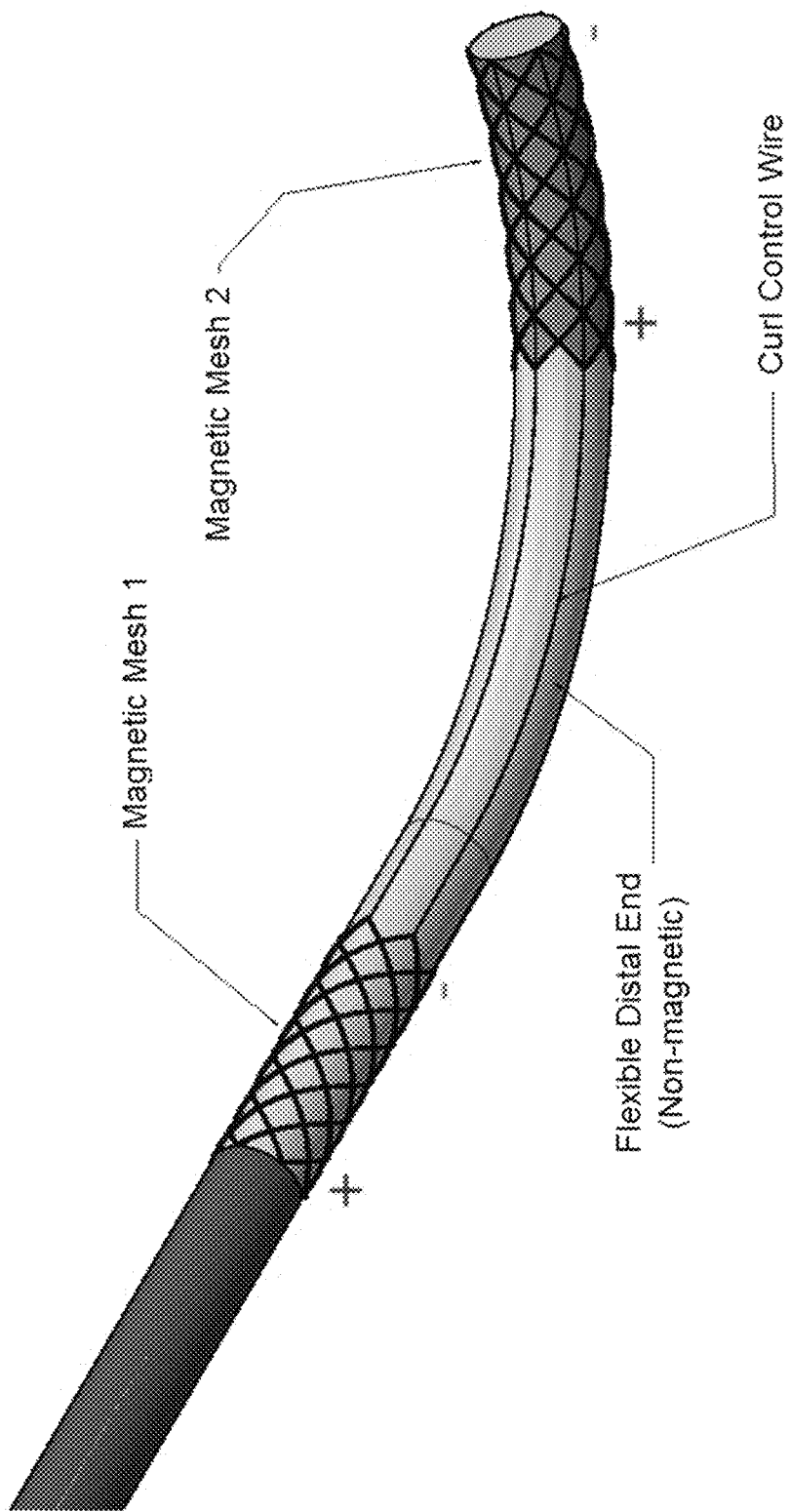
FIG. 8 illustrates an example of a catheter similar to that shown in FIG. 7 with two permanent magnets, separated by a flexible wire section.

In some embodiments, the catheter guidewire is itself permanently magnetized so that one or more sections of the guidewire become the permanent magnets in the system. This can be a section of stainless steel mesh integrated with the catheter guidewire (as illustrated in FIGS. 7 and 8 that show the one and two magnet variations, respectively). This embodiment provides a very compact footprint for the on-device permanent-magnets, as no additional material is added beyond what would already be present in a conventional guidewire. In some embodiments, the magnetized catheter guidewire sections are stainless steel.

Example Prototypes

Figure 9A:
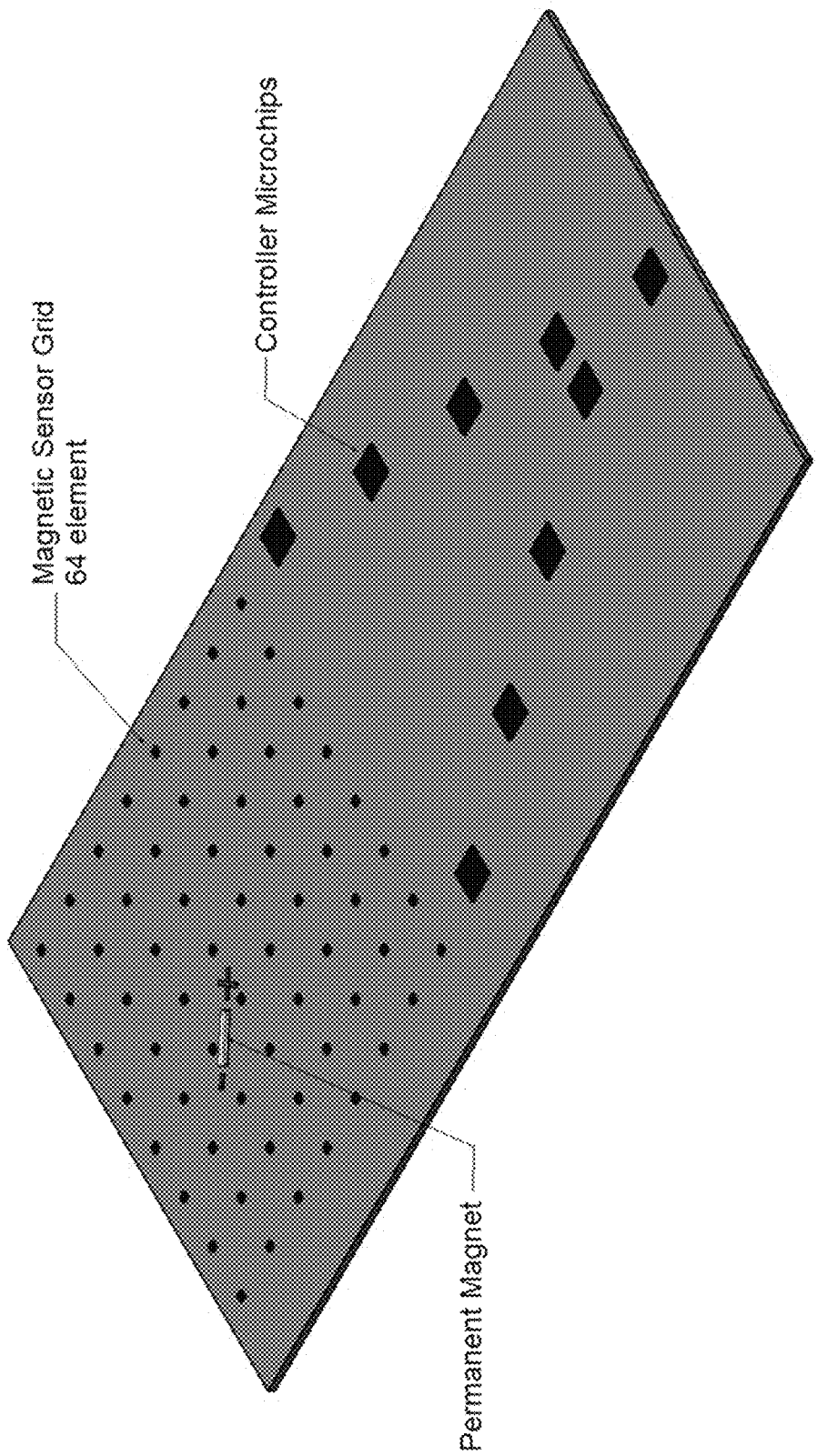
FIGS. 9A and 9B illustrate an example of a single magnet medical device interacting with a system comprising a sensor array, a data acquisition module, a signal processor and a display.
Figure 9B:
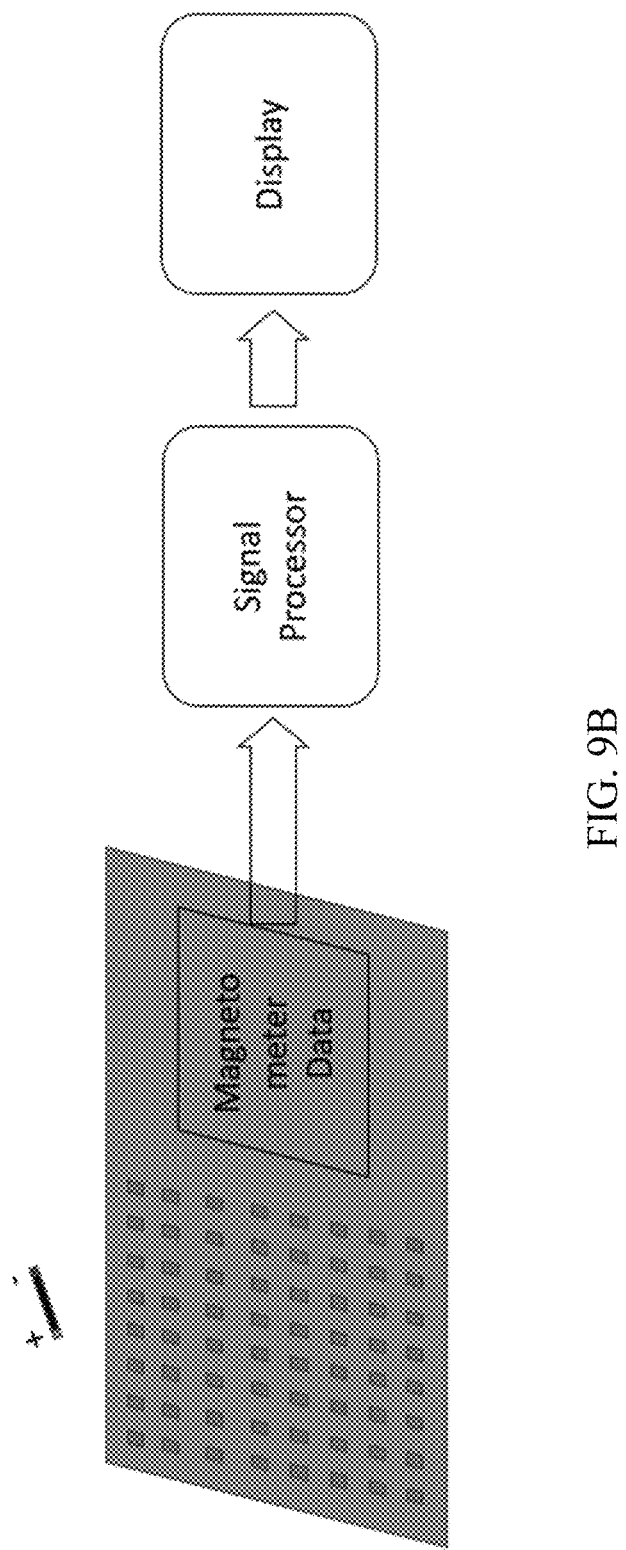

FIG. 9A illustrates a permanent dipole magnet interfacing with the prototype system that includes the microchip controllers and the 64-element (8×8) grid of sensors. FIG. 9B shows the microcontroller chips being configured to collect the magnetometer data and pass it to a signal processor comprising one or more computational modules (described in further detail below), which estimates the position and orientation of the medical device, and provides this information to a user using the display illustrated in FIG. 9B.

Figure 10A:
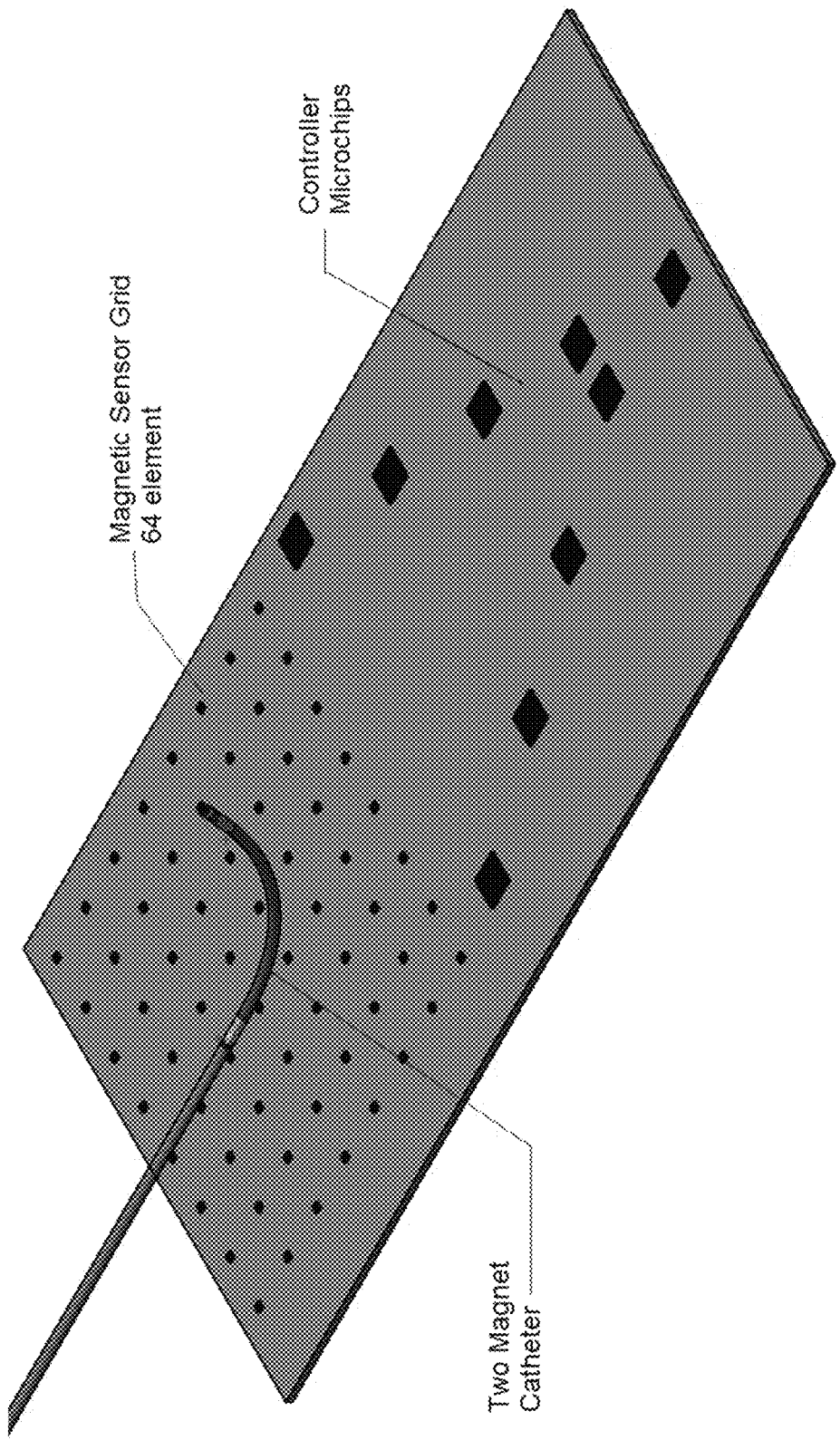
FIGS. 10A and 10B illustrate an example of a two-magnet medical device interacting with a system comprising a sensor array, data acquisition module, signal processor and display.
Figure 10B:
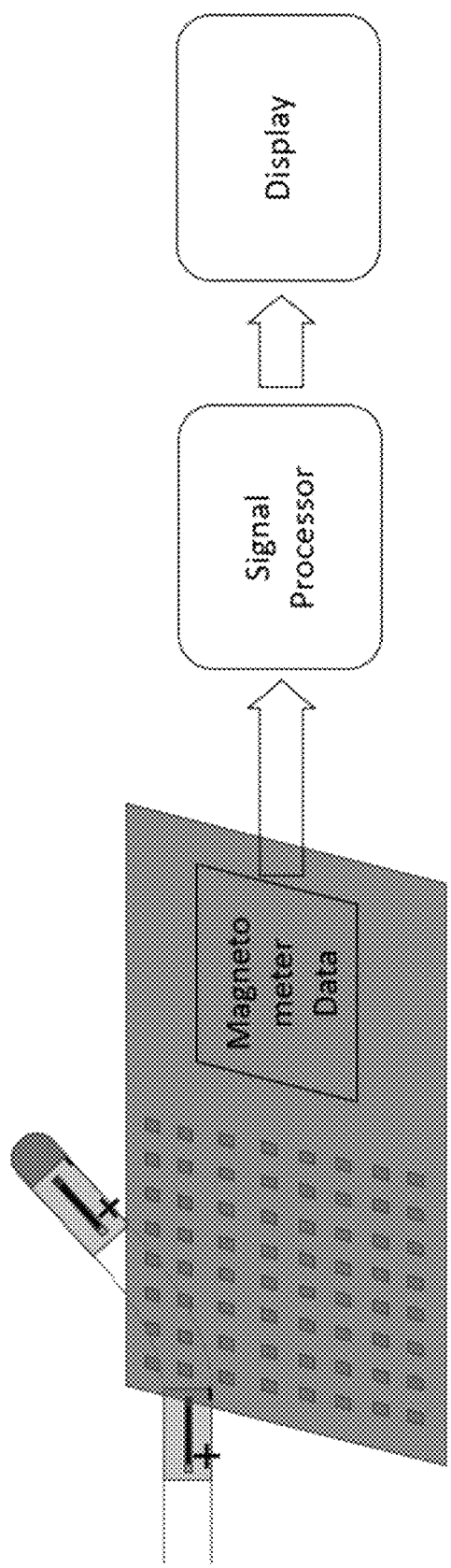

FIGS. 10A and 10B are similar to the framework illustrated in FIGS. 9A and 9B, and illustrate a two-magnet medical device interfacing with the prototype system.

Figure 11A:
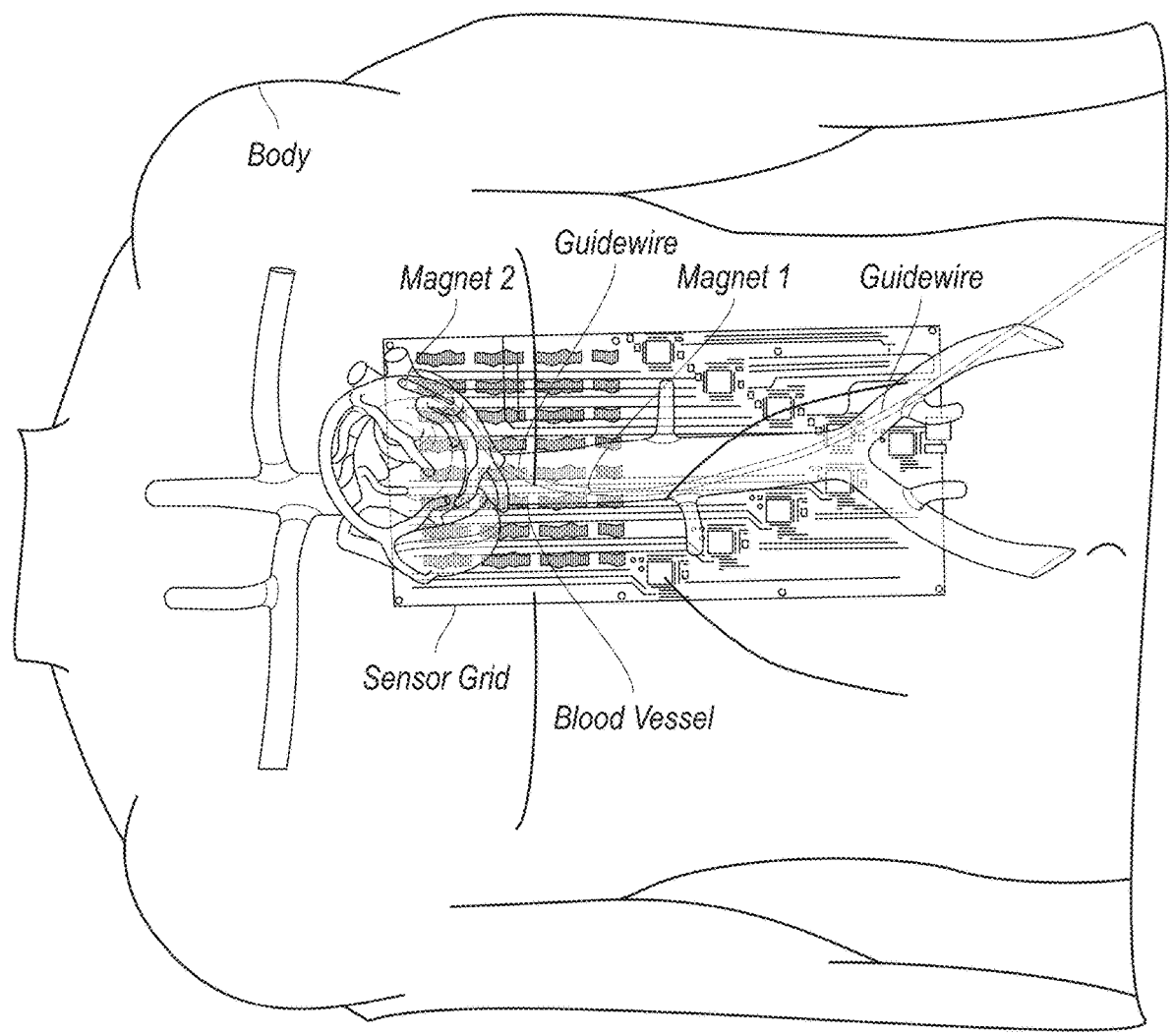
FIGS. 11A and 11B illustrate a top-view and side-view of a two-magnet catheter guidewire in a blood vessel, showing the patient organ system and patient boundary, and the sensor grid, respectively.
Figure 11B:
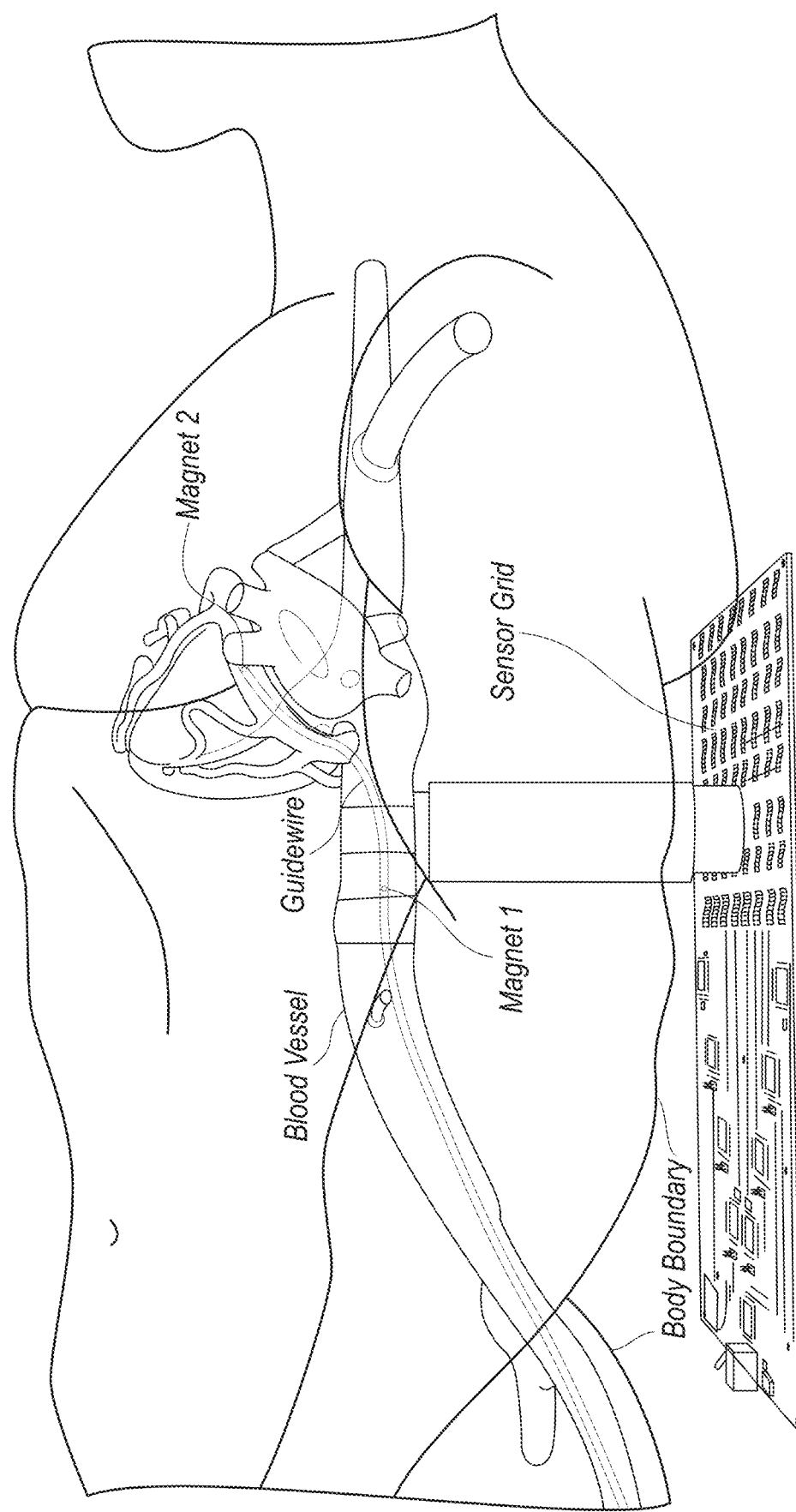

FIGS. 11A and 11B illustrate a top-view and side-view, respectively, of a two-magnet catheter guidewire in a phantom blood vessel, showing the patient organ system and patient boundary, and the sensor grid. A system for estimating the position and orientation of an invasive surgical device, e.g., the illustrated catheter guidewire with two permanent magnets, relative to a reference frame, comprises:
 (1) one or more permanent magnets mounted on the surgical device;
 (2) multiple magnetometer sensors at fixed locations (e.g., forming a sensor grid and providing a reference frame);
 (3) the multiple magnetometer sensors can be configured to perform magnetic field measurements of the direct current (DC) superposition field of the one or more permanent magnets; and
 (4) one or more processors for receiving the input signals and calculating the position and orientation of the one or more permanent magnets mounted on the surgical device.

Examples of Computational Modules for the Disclosed Technology

Figure 12:
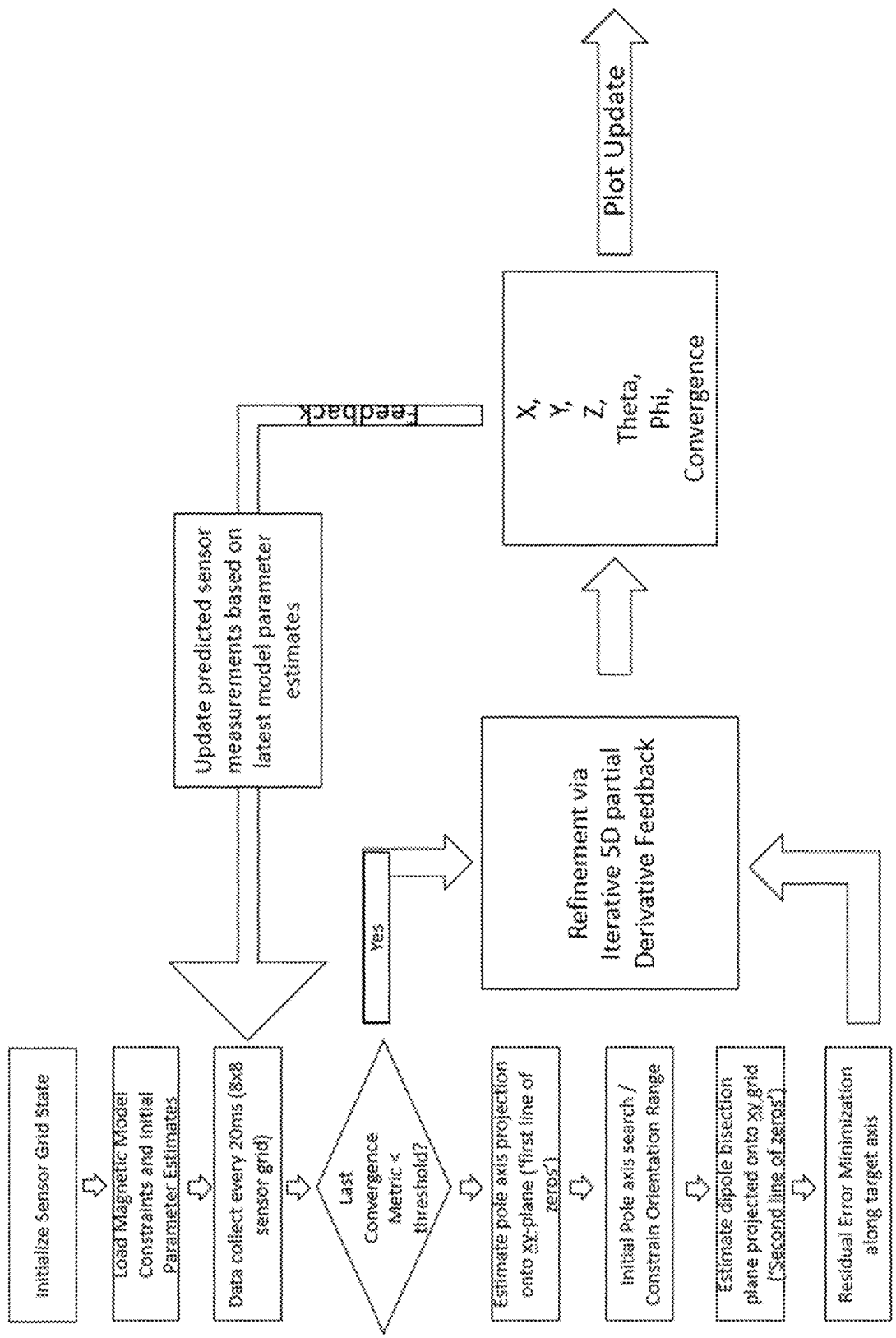
FIG. 12 is an example flow diagram for magnet localization using a single magnet.

FIG. 12 is a flow diagram of an example method for localization of a single permanent magnet. As illustrated therein, the localization procedure for a medical device comprising a single permanent magnet begins with initializing the sensor grid state, and loading the magnetic model constraints and initial parameter estimates. In an example, the data collection rate for an 8×8 sensor grid is every 20 ms. In some embodiments, each datum that is collected may be processed. In other embodiments, the collected data may be downsampled (or upsampled) prior to processing.

If the most recently computed convergence metric is less than a predetermined threshold, then the refinement procedure (further detailed in FIG. 15) is performed. If not, then the following series of operations (which constitute the geometric feature extraction process that is detailed later in the document) are performed prior to performing the refinement procedure:
 (a) the "first line of zeros" is estimated;
 (b) the initial pole axis search is performed with a constrained orientation range;
 (c) the "second line of zeros" is estimated; and
 (d) the residual error minimization along the target axis is performed.

The refinement procedure is followed by estimating the model parameters (e.g., x, y, z, theta and phi) and the convergence metric. The estimated parameters are displayed as well as used to update the predicted sensor measurements in the feedback path illustrated in FIG. 12.

Figure 13:
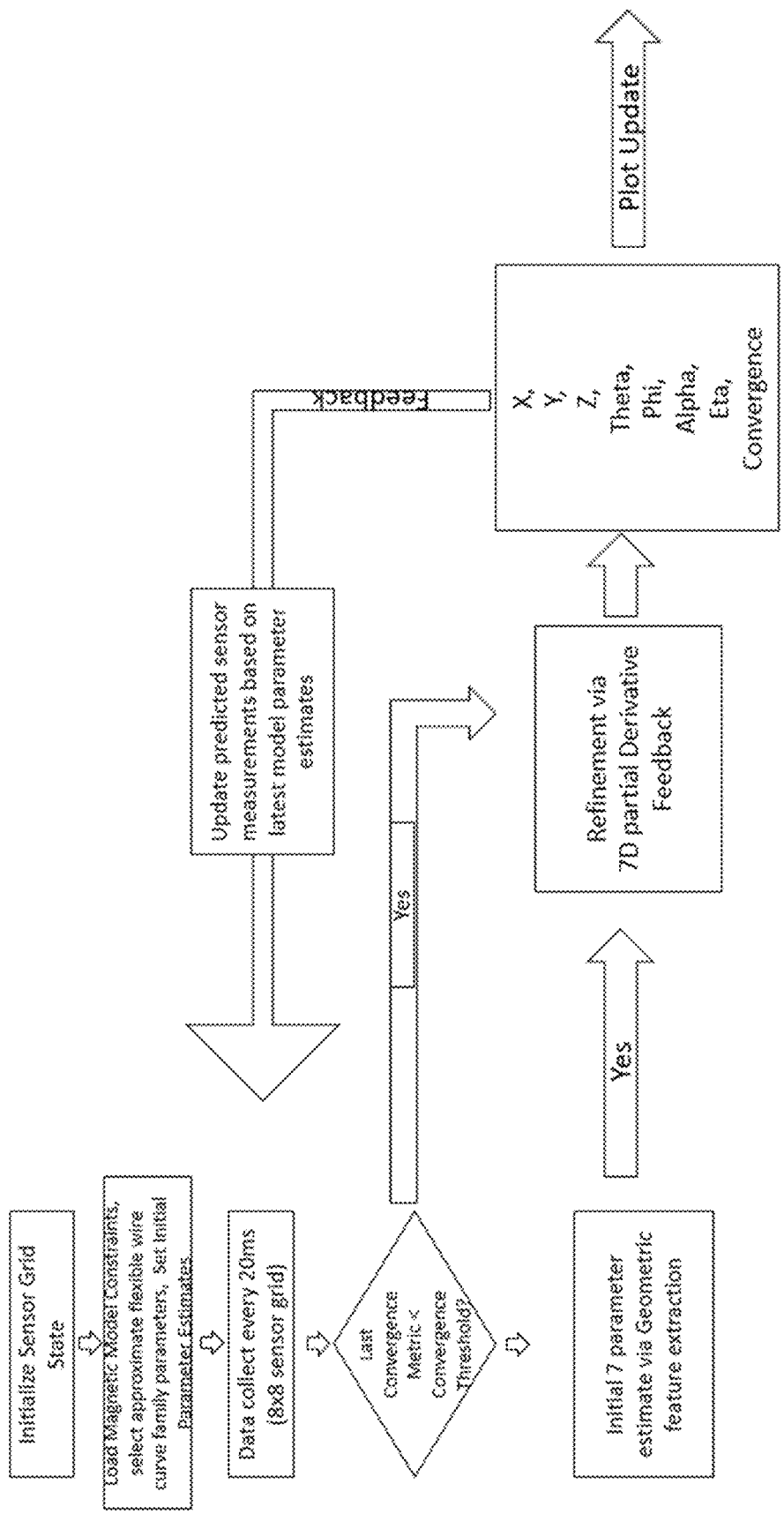
FIG. 13 is an example flow diagram for magnet localization with multiple magnet that uses a precise rotational compliance model.

FIG. 13 is a flow diagram of an example method for localization of multiple (two or more) permanent magnets (N≥2) with an exact rotational compliance model. The flow diagram in FIG. 13 is similar to the flow diagram described for the single-magnet system in FIG. 12. However, in contrast to the single-magnet system that uses a 5-parameter model, a 7-parameter model (that includes the additional parameters alpha and eta) is used for the geometric feature extraction and refinement procedures.

Figure 14:
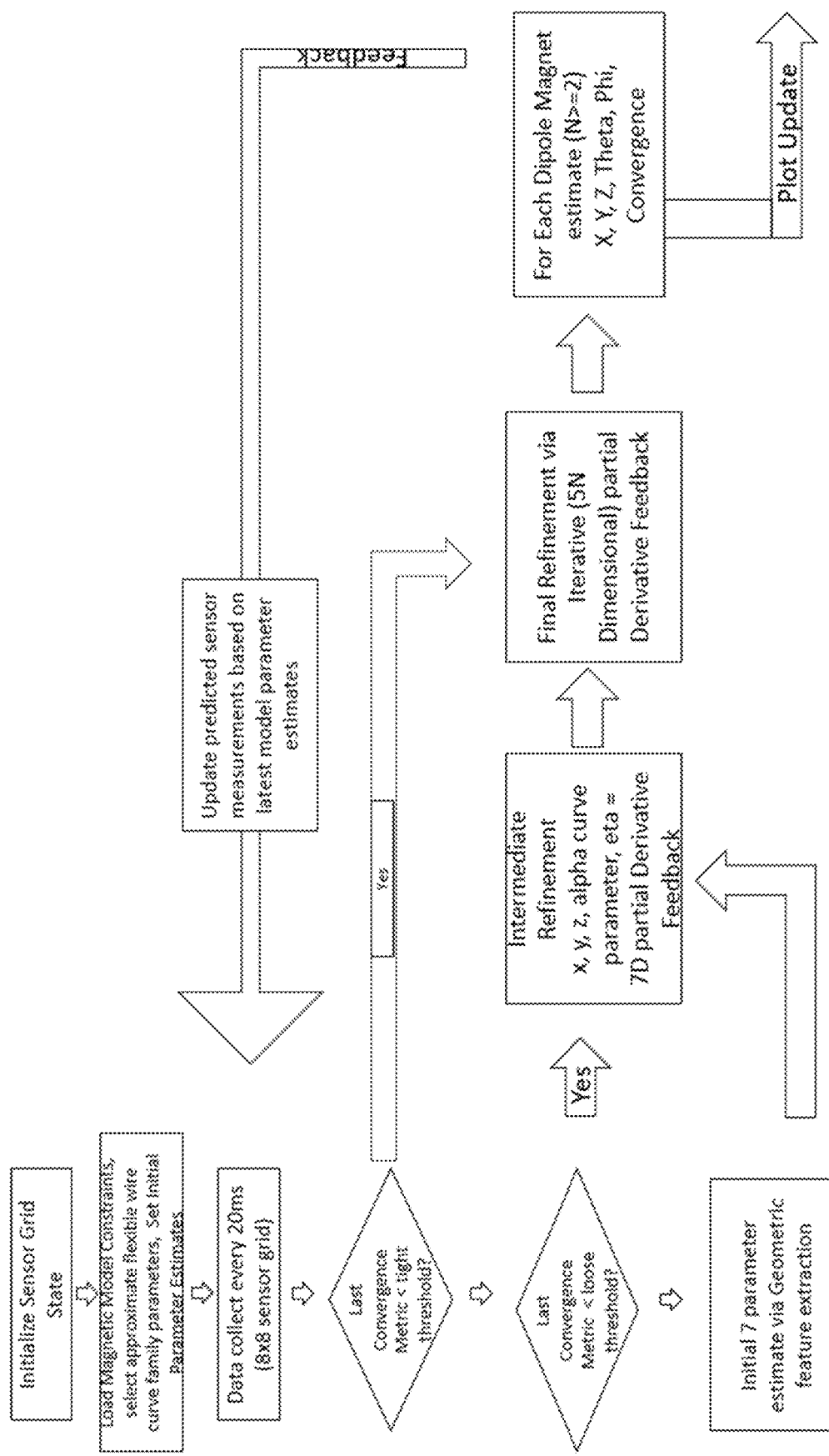
FIG. 14 is an example flow diagram for magnet localization with multiple magnet that uses an approximate rotational compliance model.

FIG. 14 is a flow diagram of an example method for localization of multiple (two or more) permanent magnets (N≥2) with an approximate rotational compliance model as an intermediate step, followed by a 5×N-dimensional refinement stage. Both flow diagrams in FIG. 13 and FIG. 14 use a 7-dimensional refinement process based on partial derivatives. However, in FIG. 13, this refinement process provides the final estimate, while in FIG. 14, the 7-dimensional refinement output is an intermediate step (that is referred to as an intermediate stage in this example) and is followed by a 5×N-dimensional refinement stage that also uses partial derivatives. This enables parameter estimation of the 5-parameter model for each dipole magnet of the N magnets.

Figure 15:
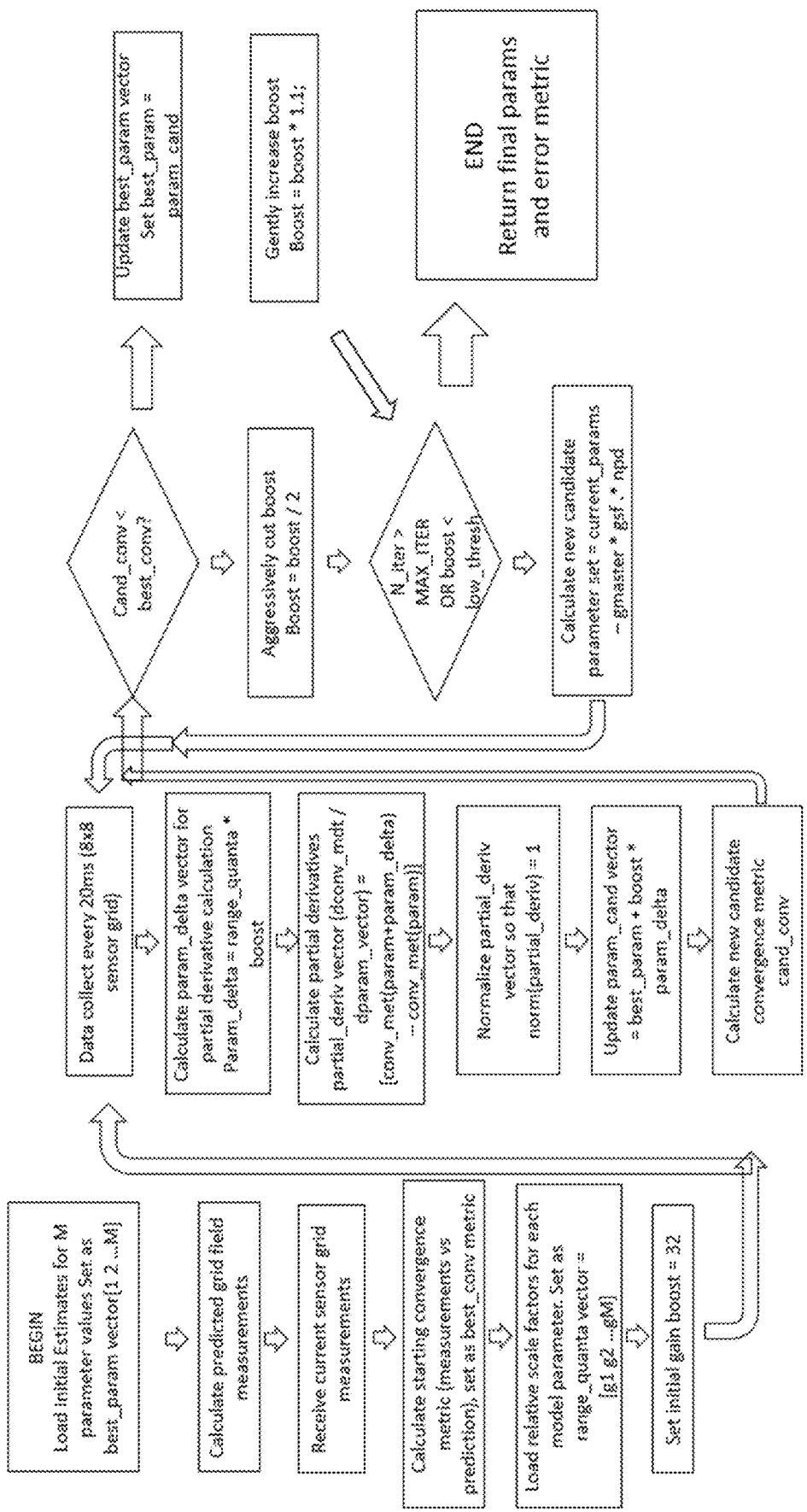
FIG. 15 is an example flow diagram for a refinement process used in magnet localization that uses M parameters.

FIG. 15 is a flow diagram of an example method for the refinement stage with M parameters, and is detailed later in the document.

According to some embodiments, operations in the flow diagrams illustrated in FIGS. 12-15 include:
 (1) Magnetic field measurements taken at each sensor within the sensor array.
 (2) Removal of earth and environmental magnetic field from each set of sensor measurements. In an example, for improved accuracy, each magnetometer can be individually calibrated with 6- or 10-parameter calibration for hard and soft iron impairments.
 (3) An approximate initial solution based on the measurement of geometric parameters of the system.
  (a) In some embodiments, specific features corresponding to system geometry are found within the sensor array data, leading to initial position and orientation estimates. This approach applies to systems with one or more permanent magnets.
  (b) In some embodiments, a best fit for the one or more permanent magnets is determined from a look-up table.
  (c) In some embodiments, the geometric features and table lookup method position and orientation estimates are blended.
 (4) Generating a parameterized model representing estimated permanent magnet position parameters.
  (a) In some embodiments, e.g., illustrated in FIG. 12, the model has 5 parameters, representing x, y, and z position of a single cylindrical dipole magnet plus azimuth and elevation. In the case of a cylindrical magnet, the rotation about the magnet axis does not change the resulting magnetic field, so this parameter does not need to be modeled. By the convention chosen, for zero theta (yaw rotation about z-axis), the magnetic poles are aligned in the sensor reference frame x-direction, with x position of the positive magnetic pole less than the x position of the negative magnetic pole.

(b) In some embodiments, e.g., for two permanent magnets with a hinge between them as illustrated in FIG. 5, the model has 7 parameters, representing x, y, and z, theta and phi positions of one permanent magnet with a rigid section leading to hinge, the sixth parameter being the deflection angle of the hinge, and the seventh parameter being the rotation angle about the first magnet axis.

(c) In some embodiments, in the context of FIGS. 13 and 14, two or more permanent magnets may be mounted on a flexible section of guidewire, wherein the shape of the guidewire matches a circular arc-segment, which has constant curvature along the flexible section of the wire. In this case, the angle of bend of the guidewire is proportional to the cumulative path length along the flexible section of guidewire. Over this section with constant curvature constraint, the orientation of the mounted or incorporated permanent magnets is linearly proportional to the length of the wire path separating each magnet. If the constant curvature constraint is adhered to precisely, a two or more magnet system can be modeled with a 7-parameter system, including x, y, and z positions, and theta and phi values for one magnet, plus a rotation parameter eta being the rotation angle about the first magnet axis, and the seventh parameter α being the radius of curvature of the flexible section between the magnets.

(d) In some embodiments, e.g., in the context of FIG. 13, two magnets may be separated by a flexible catheter guidewire section, with only an approximate curvature constraint on the flexible guidewire section and distance constraints between the two magnets. This requires a model with 10 parameters, i.e., x, y, z, azimuth and elevation separately estimated for both magnets. Since there is an approximate curvature constraint in this embodiment, an intermediate 7-parameter optimization can be performed to give a best fit 7-parameter solution, which can be used as an input for a full 10-parameter optimization to yield x, y, z, theta and phi for each magnet independently.

(e) In some embodiments, a wire with approximate constant curvature or other modeled constraints may include three or more magnets along the flexible guidewire section. Like the two-magnet system, this system can be modeled with the same 7-parameter model including x, y, z, theta and phi for first magnet, rotation around first magnet axis, and the radius of curvature along the section between the first and last permanent magnet.

(5) Candidate model parameters can be used to predict the corresponding locations of each magnetic pole and the resulting magnetic field measurements at each sensor in the receive sensor array.

(6) A convergence metric, representing the difference between the set of field measurements at each element of the sensor array and the predicted field measurement for each element of the sensor array, can be calculated. The convergence metric is a function of the set of differences between the measured values and the predicted values.

(a) In some embodiments, the convergence metric is not a linear function.

(b) In some embodiments, the initial location estimates of position and orientation are a blend of the geometric feature analysis and the table lookup method, with the relative weights of each method determined by the convergence metric.

(7) After initial position and orientation estimates have been made, precise estimates are made using a refinement stage (e.g., illustrated in FIG. 15) which successively updates the best candidate model parameters using the set of partial derivatives of the convergence metric relative to changes in each parameter, such that the system attempts to drive the convergence metric toward zero.

(a) In some embodiments, the absolute magnetic field strengths of the permanent magnet or magnets are used in the convergence metric.

(b) In some embodiments, the measured and predicted magnetic fields are normalized relative to each other such that the total energy in the set of measured field value matches the total energy in the set of predicted field values.

(8) In the case where the amount of motion from one snapshot in time to the next is small, the initial geometric estimator can be skipped, and the system can proceed directly to the refinement stage. This is analogous to the continuous tracking mode following initial acquisition for a GPS navigation system.

(a) In some embodiments, the choice of whether to perform full position acquisition or continue with tracking mode is made by calculating the convergence metric between the last estimated location and the new set of measurements. The tracking mode is used if this metric is below a threshold.

Example Validations and Experimental Results

Figure 16:
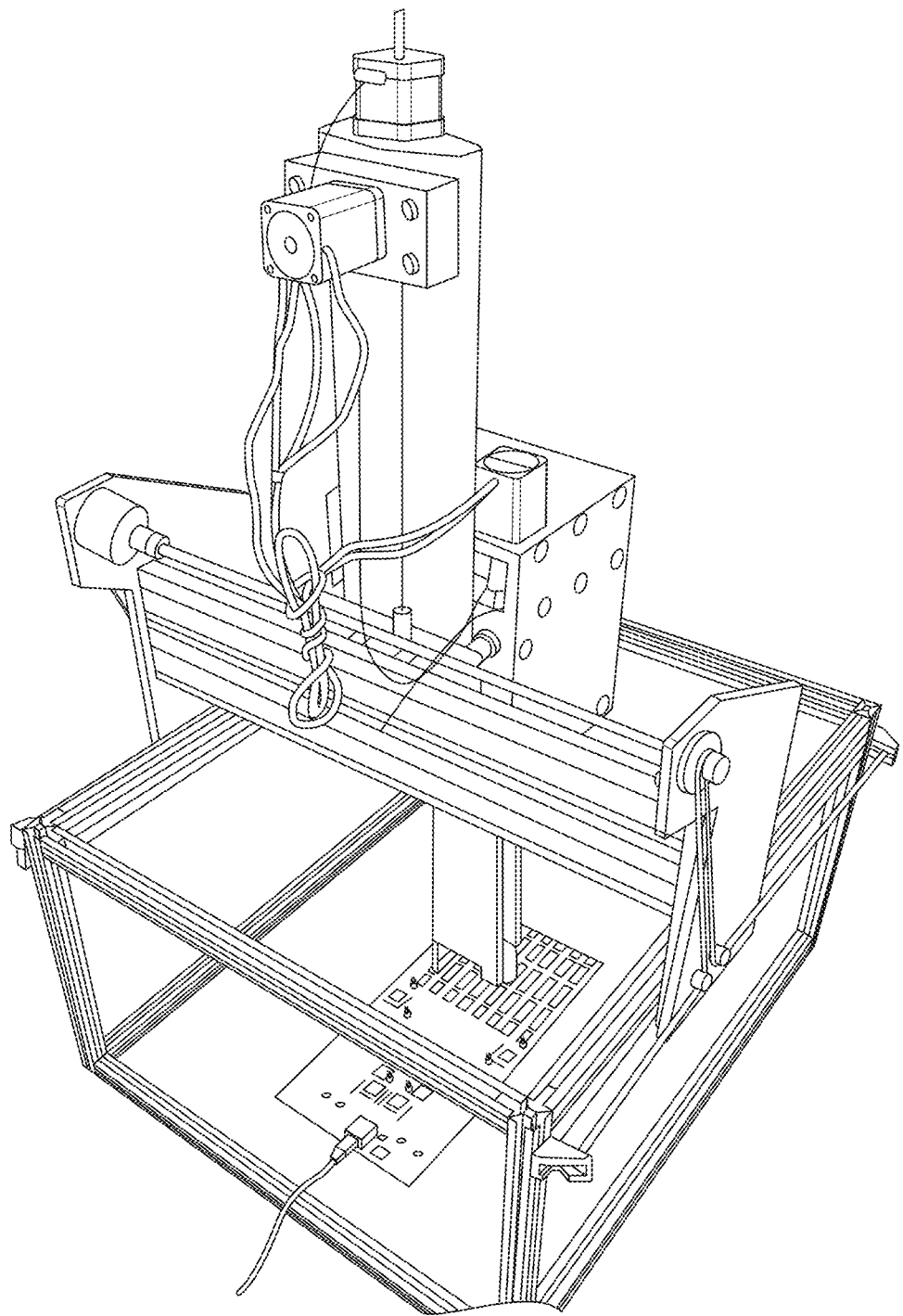
FIG. 16 illustrates an example of a gantry robot for validating a single magnet localization system.
Figure 17A:
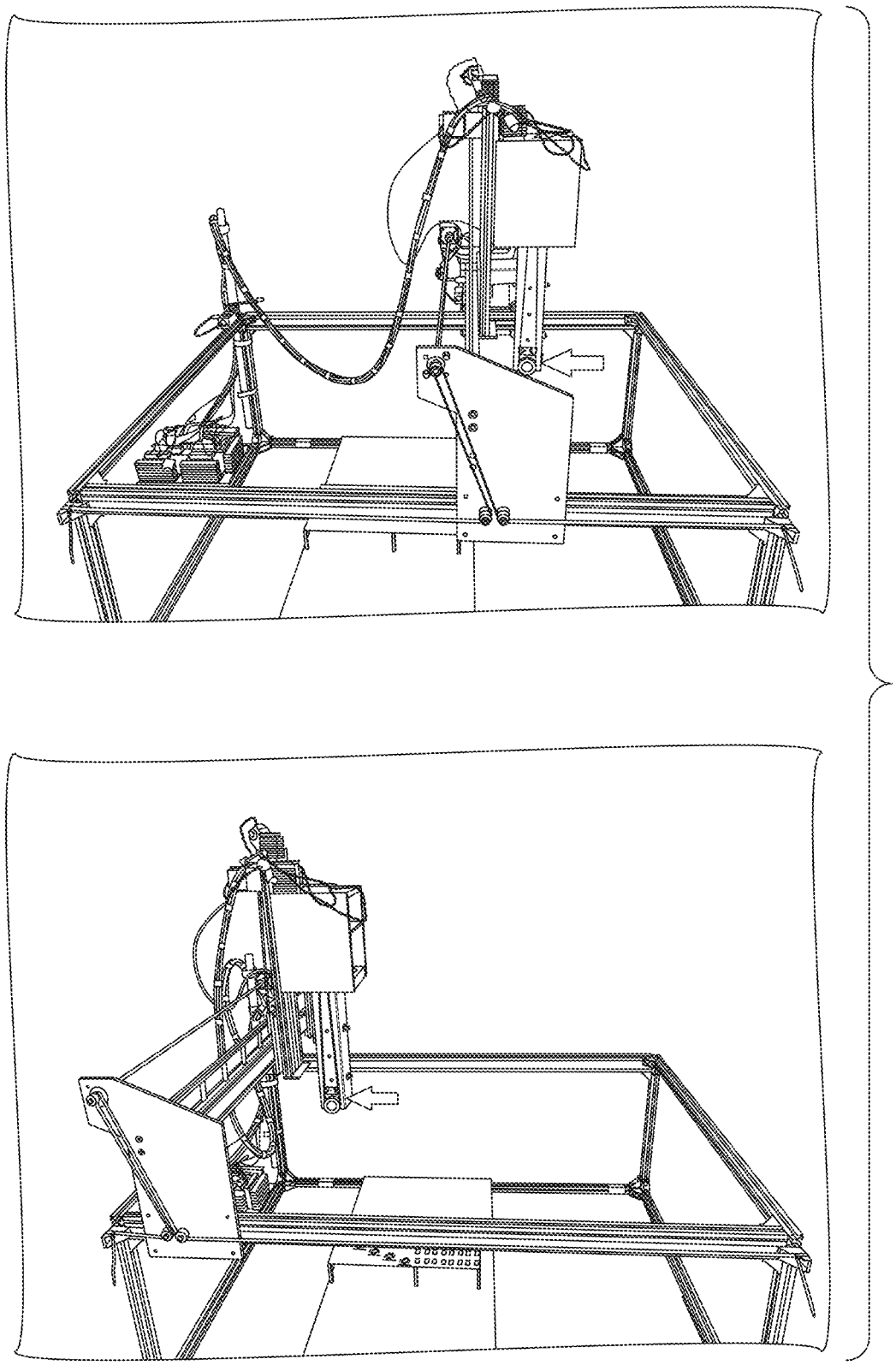
FIG. 17A illustrates an example of X-axis motion for the gantry robot in FIG. 16.
Figure 17B:
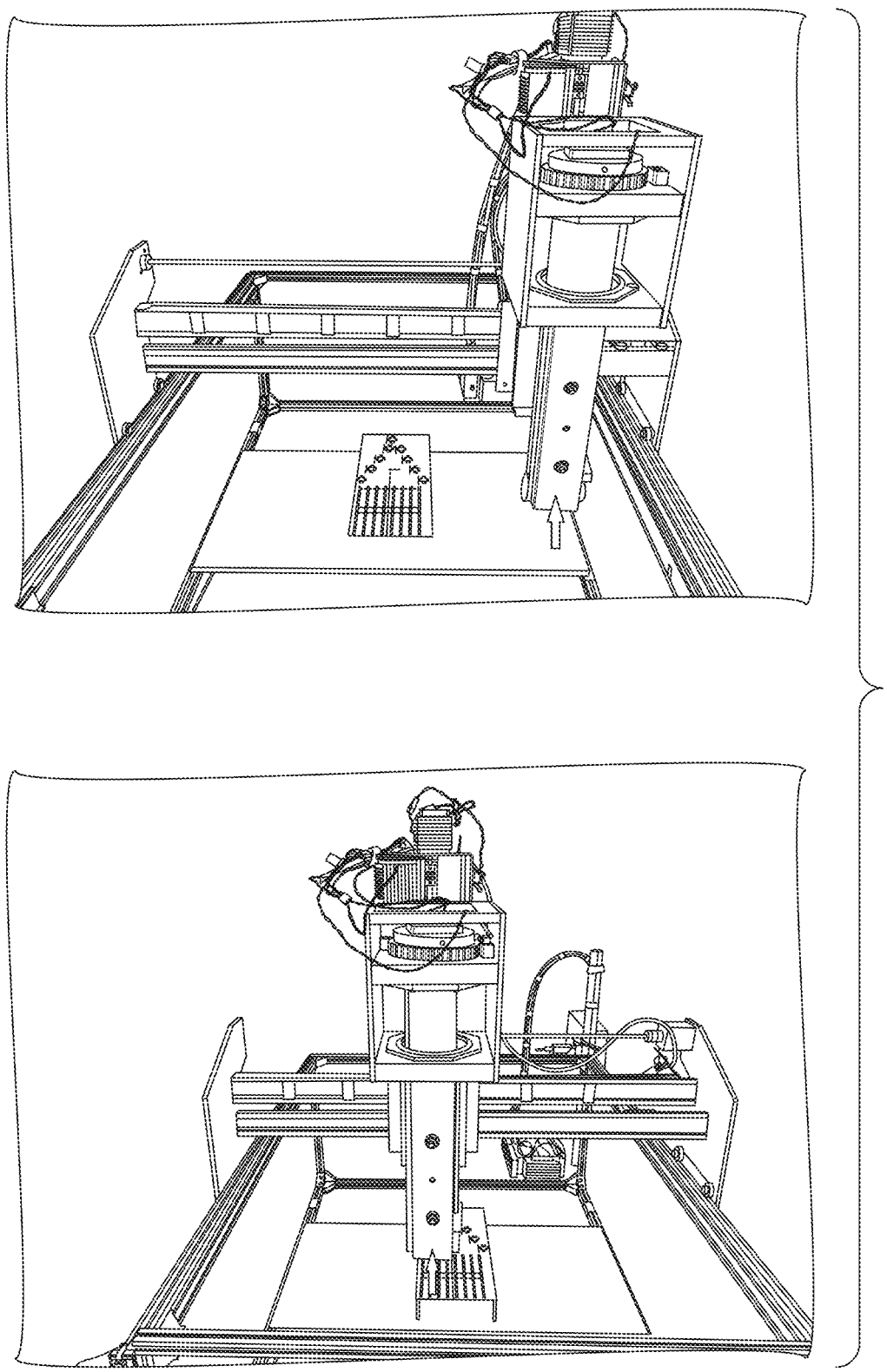
FIG. 17B illustrates an example of Y-axis motion for the gantry robot in FIG. 16.
Figure 17C:
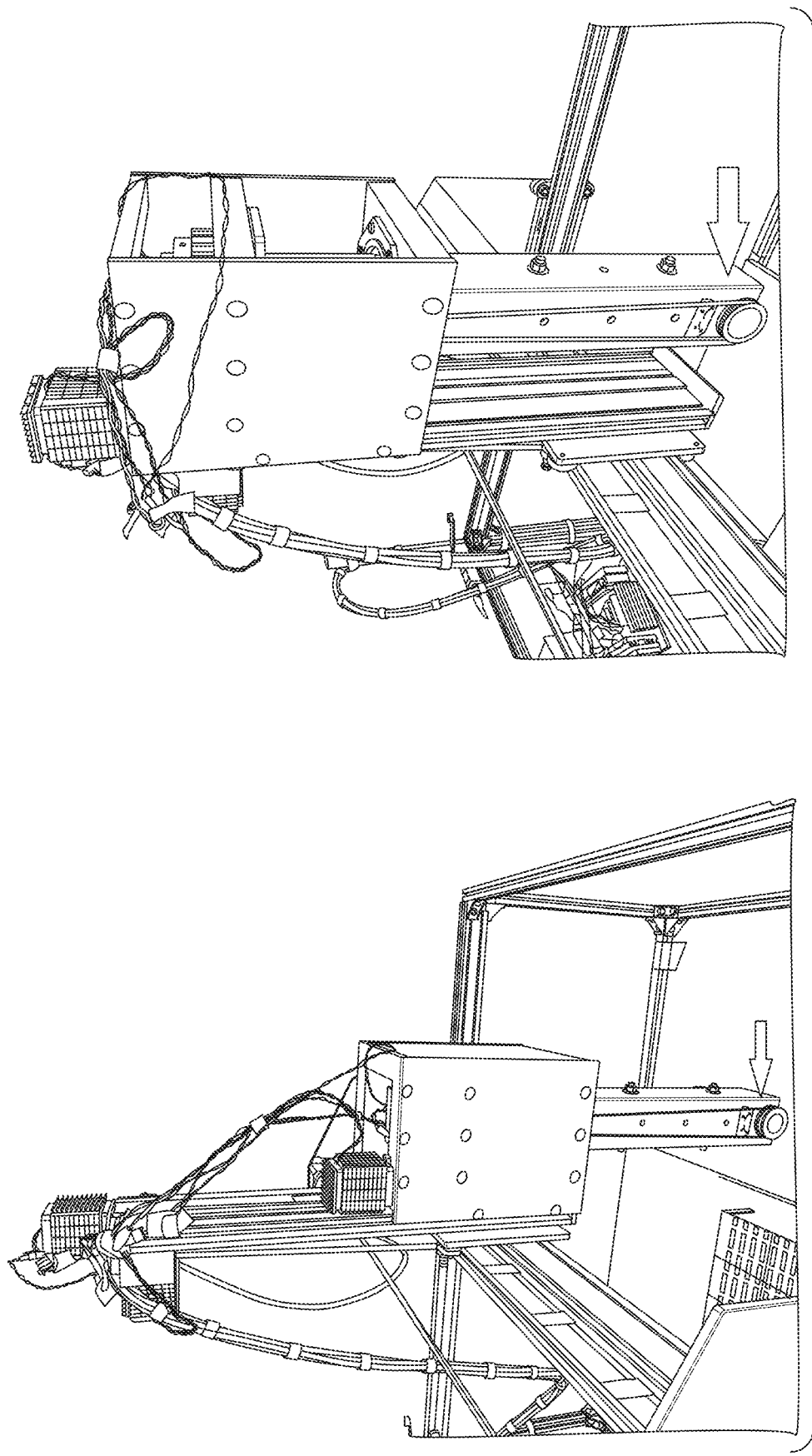
FIG. 17C illustrates an example of Z-axis motion for the gantry robot in FIG. 16.
Figure 17D:
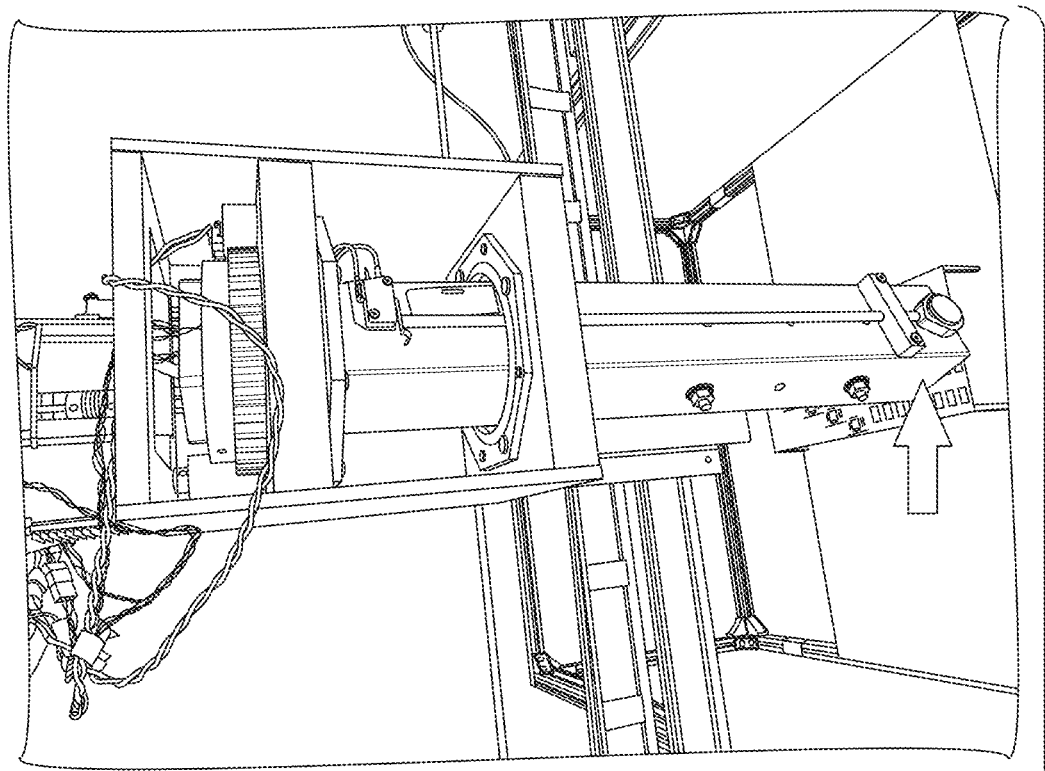
FIG. 17D illustrates an example of θ-axis motion for the gantry robot in FIG. 16.
Figure 17D:
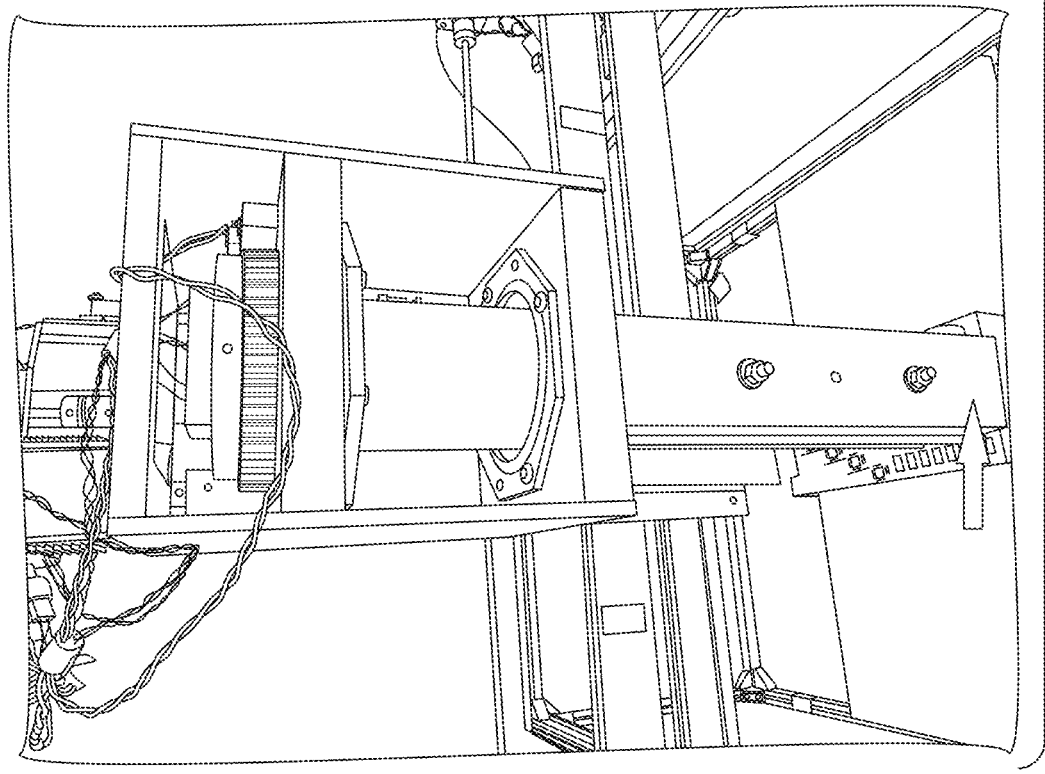
Figure 17E:
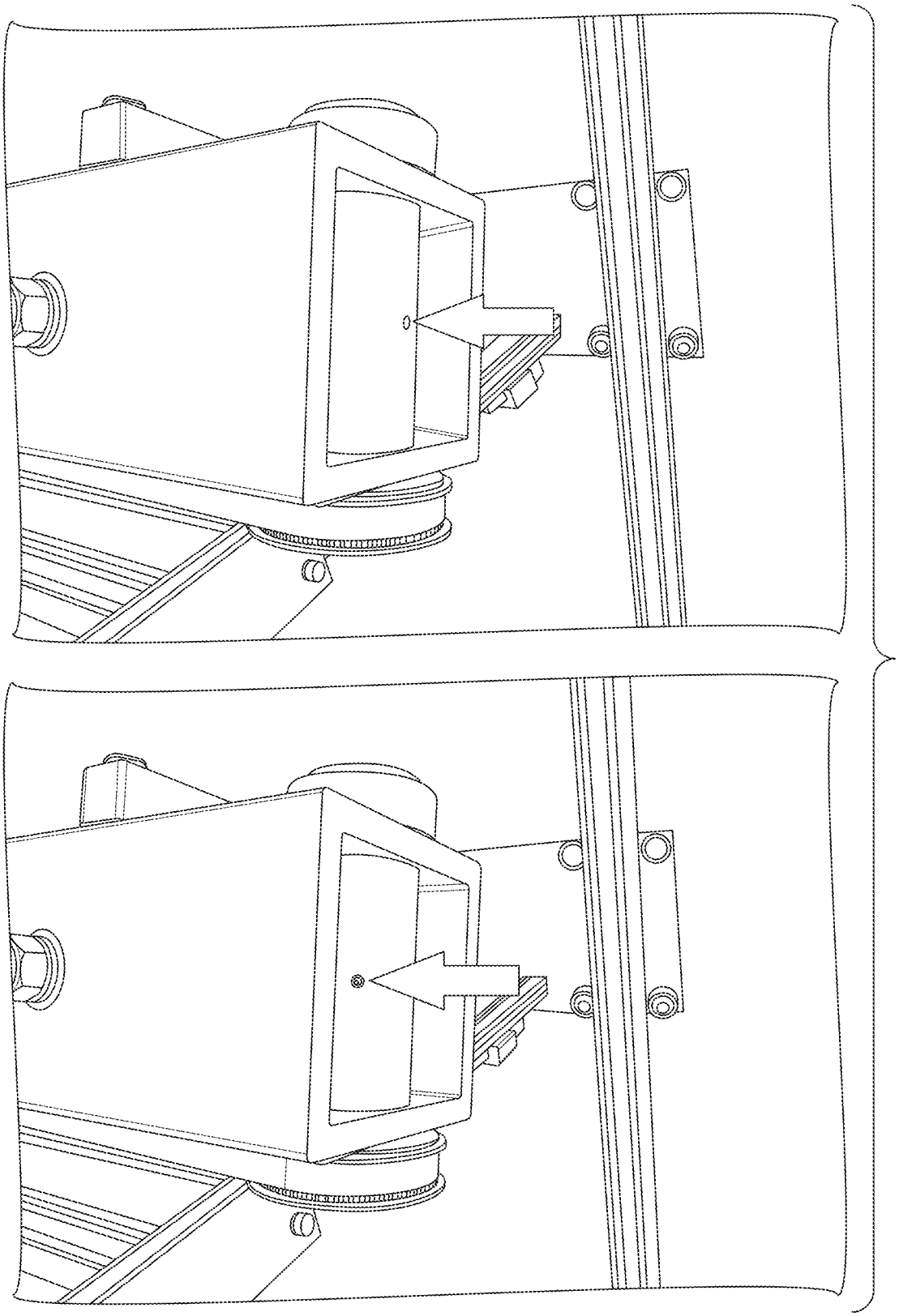
FIG. 17E illustrates an example of ϕ-axis motion for the gantry robot in FIG. 16.

Single magnet system. Single magnet accuracy was validated using a gantry-style robot (as illustrated in FIG. 16) with 5 degrees of freedom. Independent control was provided for x, y, and z positions for the magnet geometric center (illustrated in FIGS. 17A, 17B and 17C, respectively), along with theta rotation about sensor z-axis (illustrated in FIG. 17D) and rotation of a cylinder containing the magnet to achieve desired tilt relative to the sensor x-y plane (illustrated in FIG. 17E). A hole was drilled within the central cylinder leaving space for the dipole magnet, which is installed in the geometric center of the cylinder. Individual set screws on each side are used to complete the central alignment of the dipole magnet within the cylinder.

Figure 18A:
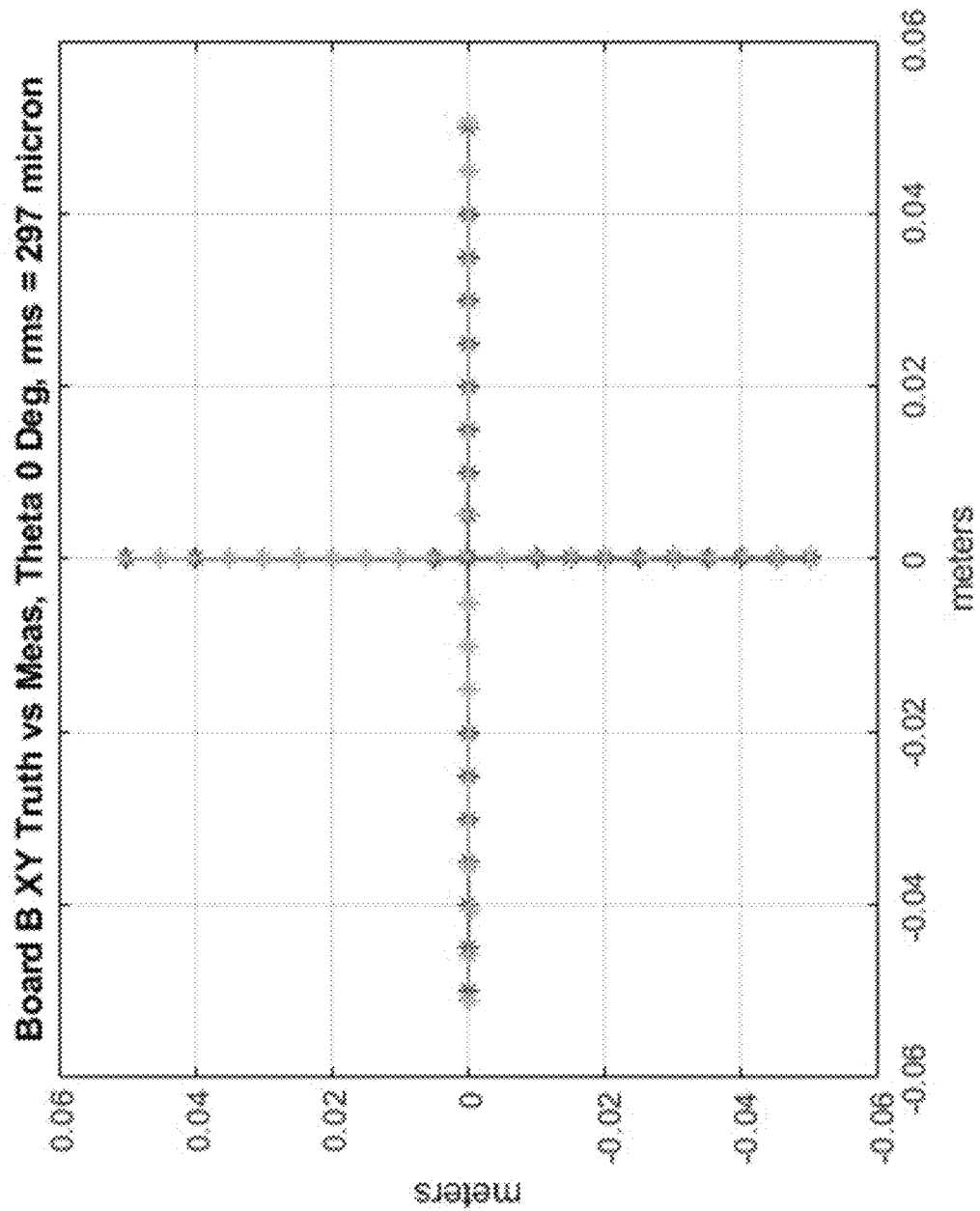
FIGS. 18A and 18B illustrate validation plots for the gantry robot in FIG. 16 for θ=0 and θ=45, respectively.
Figure 18B:
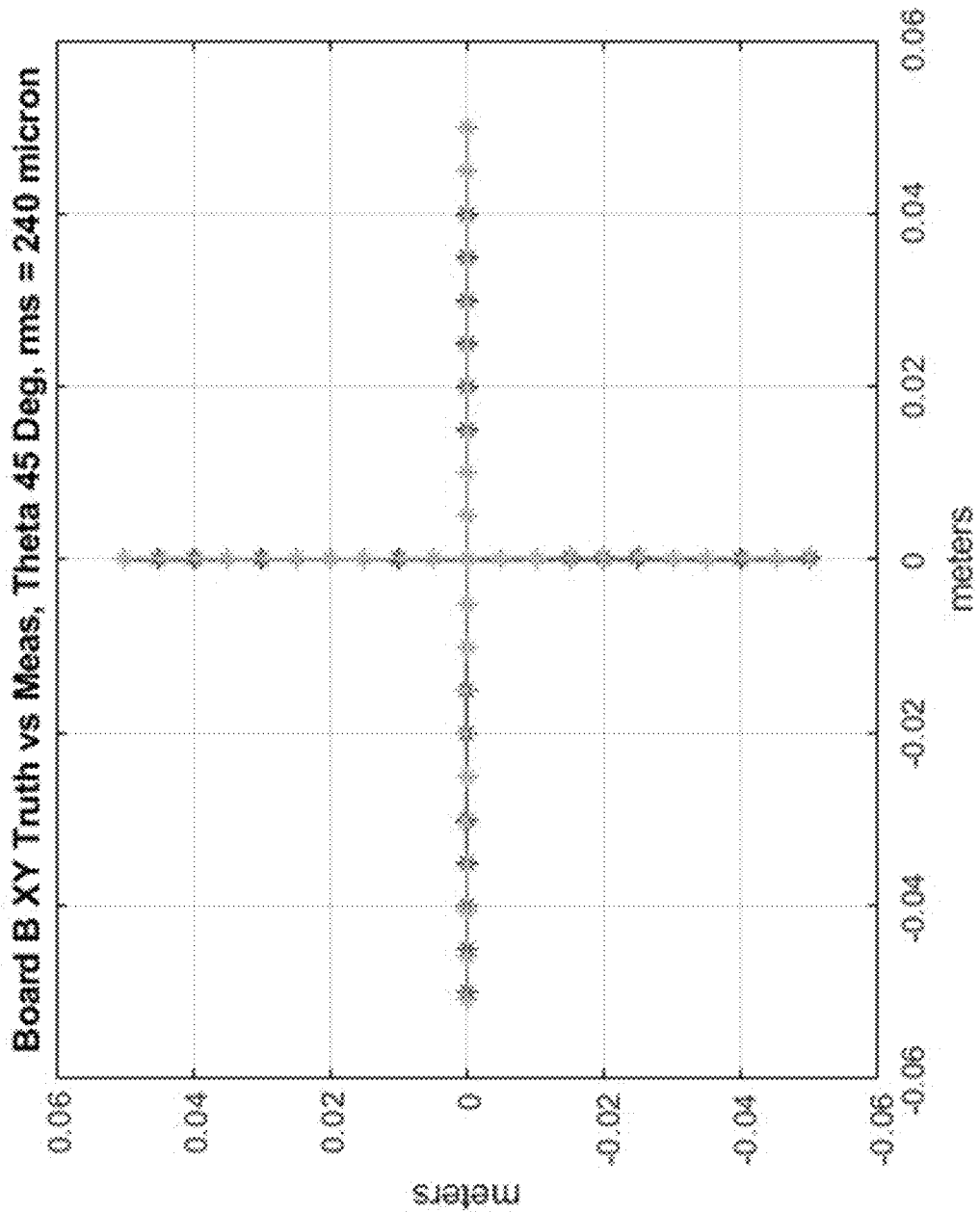

For the two single magnet plots (illustrated in FIGS. 18A and 18B), z is held constant, and positions along the x and y axis are measured with commanded position truth points separated by 5 mm. For plot in FIG. 18A, the theta rotation angle about the sensor z axis is 0 and for the plot in FIG. 18B, the theta rotation angle about the sensor z axis is 45 degrees. For these two test cases, the 3D root mean square (RMS) error in position was measured to be 240 microns and 297 microns, respectively. In the plots, the truth points are marked in green and the measured points are marked in orange.

Figure 19A:
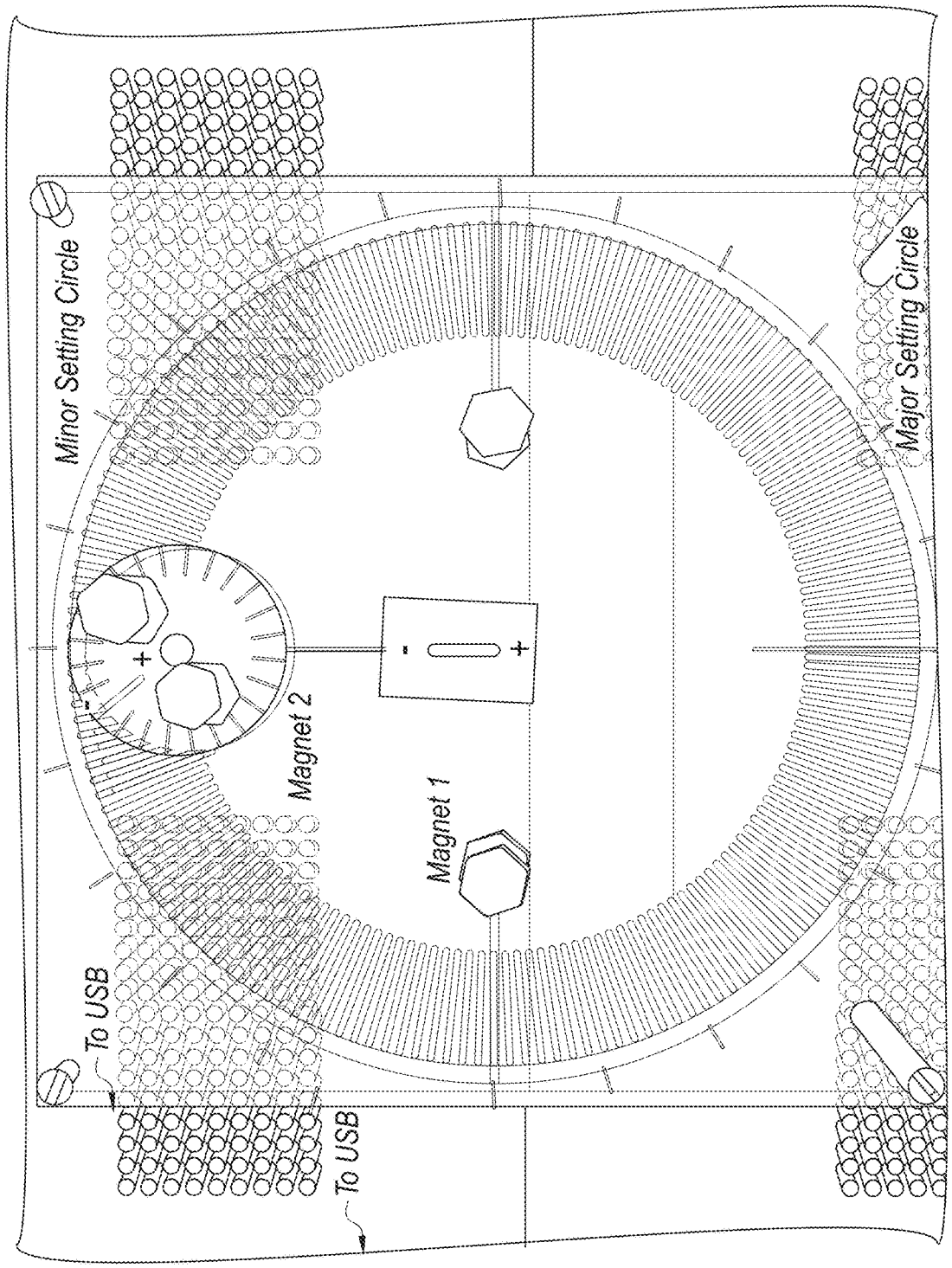
FIGS. 19A and 19B illustrate an example of a wheel-in-wheel setup for system validation.
Figure 19B:
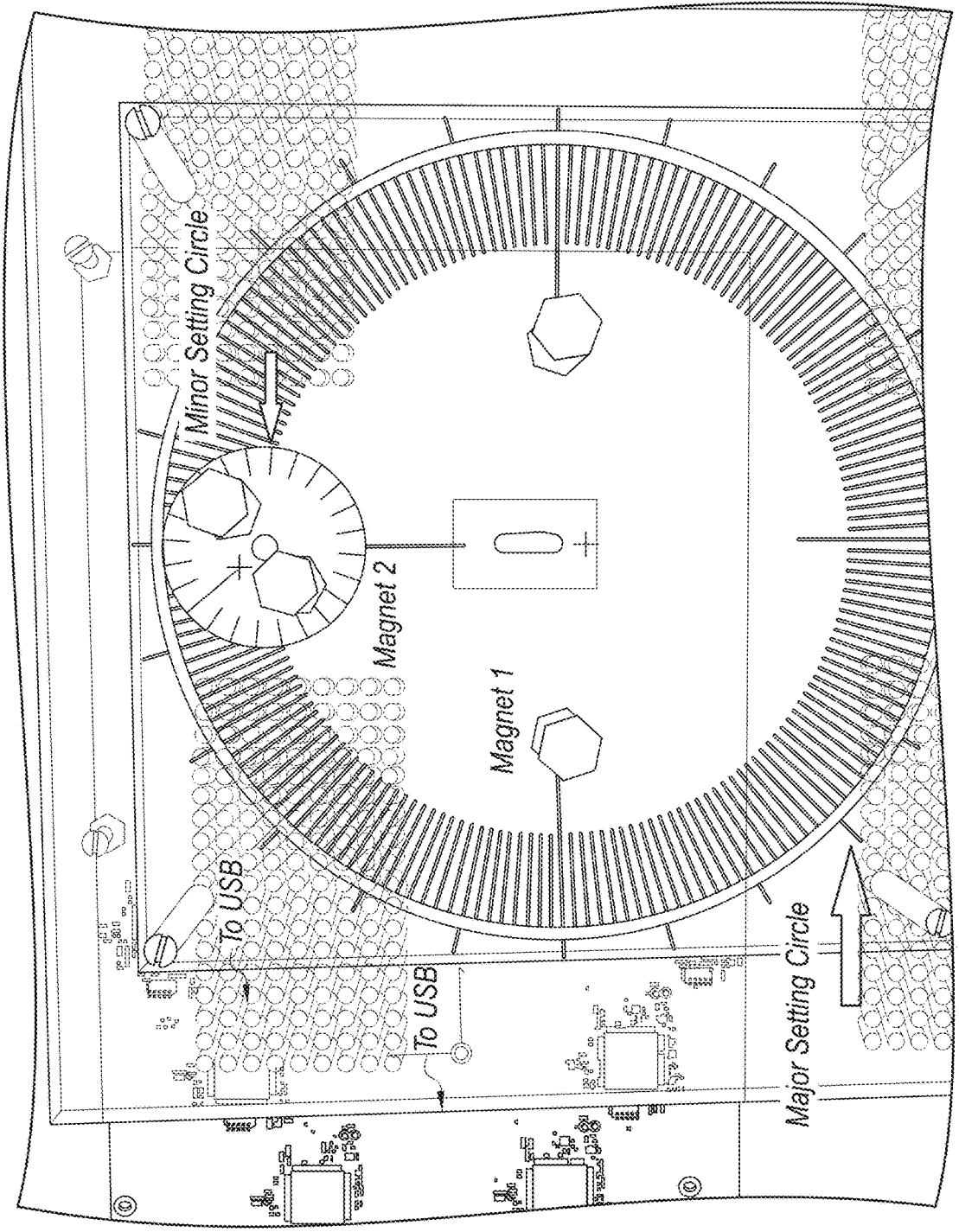

Two-magnet system. Validation of the two-magnet system was conducted using a wheel-in-wheel system (illustrated in FIGS. 19A and 19B) combined with a plug-board to precisely align position and orientation truth with the sensor grid reference frame. As illustrated therein, there are plug-board style holes at 5 mm increments to receive the set of 4 standoffs protruding from the bottom of the wheel in wheel apparatus. This provides precise alignment of the x-y position for the negative pole of the centrally mounted permanent magnet M1. With the M1 negative pole mounted directly in the center of the large circle, the circle can be rotated while the x-y position of the M1 magnet negative pole is unchanged. A second magnet is mounted inside a second smaller circle whose center lies along the magnetic axis for M1. The second magnet M2 is mounted such that the outer edge of the small circle is aligned with the positive pole of the second magnet M2. Rotation of the large circle changes location truth for the theta angle and rotation of the small circle changes location truth for the alpha deflection angle. The z-height for this system is set by adding additional sets of 4 identical height standoffs.

Figure 20:
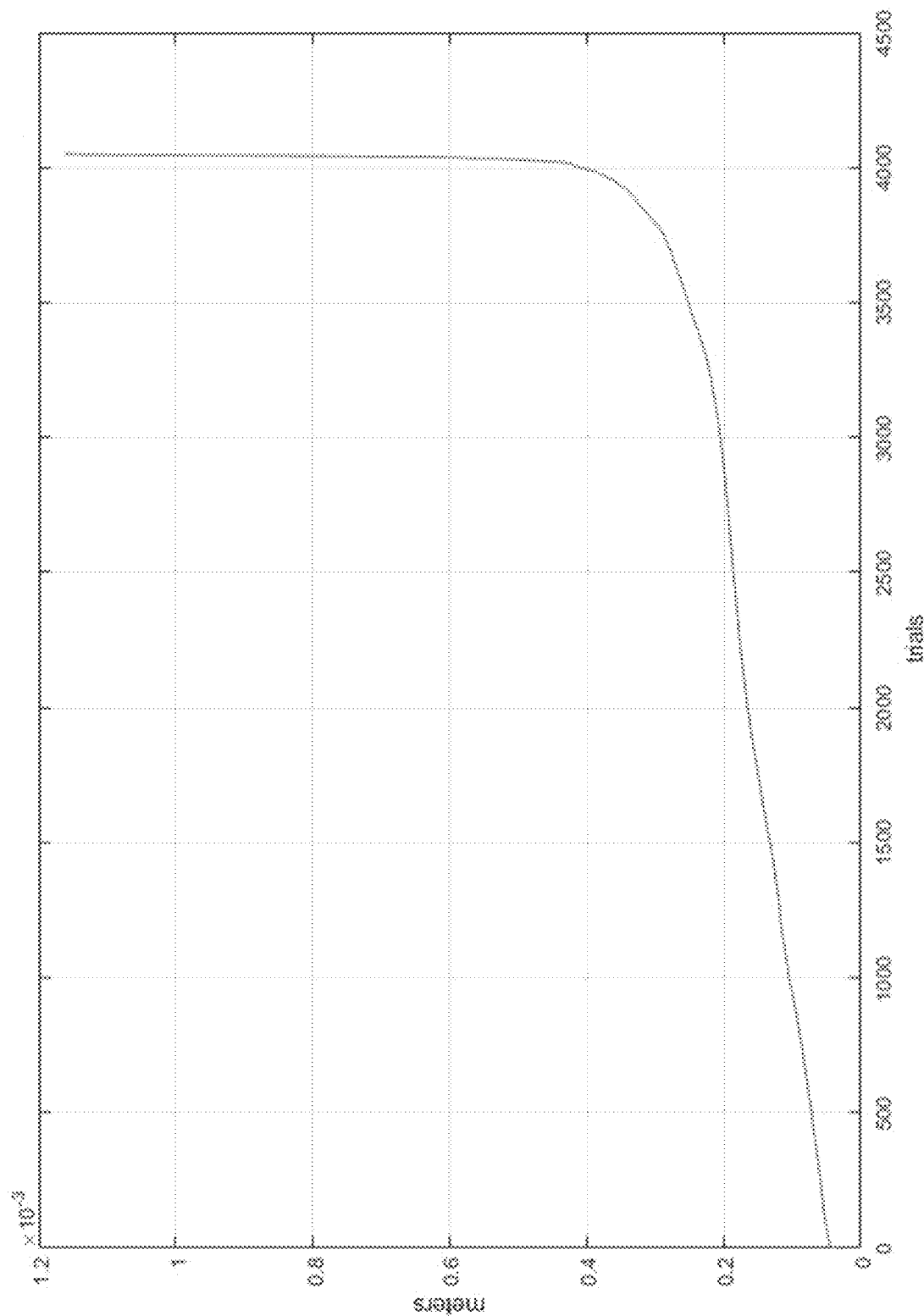
FIG. 20 illustrates an example of the three-dimensional error over 4096 trials with different orientations of the medical device.

FIG. 20 illustrates an example of the sorted three-dimensional error over 4096 trials with different orientations of the medical device. The trials were performed using a two-magnet flat test apparatus with an 8×8 grid with a 1.76 cm spacing, varying over x, y, z positions and θ, Φ, α, η angles, and which resulted in an RMS error that was measured to be 192 microns.

Additional Embodiments of the Disclosed Technology

Single-magnet system. In some embodiments, a single permanent dipole magnet is mounted on a surgical device, for example, a catheter guidewire. The guidewire is navigated within the patient to the target area (e.g., illustrated in FIGS. 11A and 11B for the two-magnet system). While the guidewire with the permanent dipole magnet moves through the patient, an array of magnetic field sensors measures the vector field components at a plurality of locations on the sensor grid. The system uses a series of increasingly precise methods to map the set of magnetic field measurements to a best fit estimate of the position and orientation parameters of the catheter guidewire mounted permanent magnet.

For the single magnet system, a close approximation for magnet x, y, and z position, theta rotation of the magnetic pole axis about the sensor z-axis (theta) and tilt of the magnetic pole axis relative to the sensor x-y plane (phi) can be calculated using geometric feature extraction methods. Once these initial approximations have been made, the estimates are passed to a refinement stage which successively improves the model parameter estimates by constructing field predictions that would arise from the model parameters, calculating an error metric of the set of differences between each field measurement and its corresponding predicted measurement at a given sensor location. The model is successively updated by following the error gradient along the set of partial differential changes in error metric as a function of each individual parameter. This refinement stage continues until convergence no longer improves or until a maximum number of iterations has been reached or exceeded.

Geometric feature extraction. For the single dipole magnet case, 5 parameters sufficiently describe both the position and orientation of the permanent magnet. The convention adopted is that position is defined by the midpoint of the magnet, equidistant from the positive and negative magnetic poles, which covers the x, y and z parameters. Additionally, angles theta and phi are used, wherein phi is pitch angle relative to the horizontal plane (x-y plane defined by the sensor grid, such that at zero phi, the z positions of the positive and negative poles are the same) and theta is a rotation about the reference z axis. For a general object in 3D space, there would be a third rotation. However, in the single magnet system, this is a rotation about the magnetic axis (line between positive and negative poles), and the measured magnetic field does not change at all in response to rotation about this axis. Thus, this parameter does not need to be included in the model.

In some embodiments, it is, in theory, possible to do a brute-force search across the 5 model parameters, but this quickly becomes computationally expensive. Large computational savings can be achieved if this 5D search can be serialized into lower-dimensional searches.

In some embodiments, this 5D search can be efficiently subdivided.
(a) In a first step, the "first line of zeros" is computed, which corresponds the best fit line project of a dipole magnetic field onto the planar sensor grid, and which is computed using a 2D search. In an example, this reduced complexity search uses an approximate pole axis search (pair of peak values for +z and −z magnetic fields). Determining the "first line of zeros" yields an estimate for the theta angle parameter and enables the determination of the line in the x-y plane that contains the x and y position values for the permanent magnet. Thus, two of the parameters are determined in this first step.
(b) The second step leverages the fact that in the plane which bisects the positive and negative pole locations for the dipole magnet, the field is identically zero. For a non-zero phi angle, it is observed that a "plane of zeros" intersects the x-y plane defined by the sensor grid as a line, and that the direction of this line is perpendicular to the first line of zeros. Herein, it can be noted that:
A line can be drawn from the x-y plane intersection point of the two features ((i) the first line of zeros and (ii) the intersection of the x-y plane with the plane of zeros) back to the dipole magnet center. The desired line is in the plane defined by the first line of zeros and the sensor z-axis.
The tilt angle relative to the z-axis can then be determined to be used to draw the line from the intersection point in x-y plane back to center of dipole magnet. If the tilt angle is correct, the magnetic field normal to both the second line of zeros and the tilted line in the plane defined by first line of zeros and z axis is uniquely zero at all points along the line. In the case of 0-tilt angle, the sensor plane intersection of the first line of zeros and the second line of zeros gives the correct x and y position of the magnet. For all other angles, the x and y position of the magnet is offset from this intersection point. The correct tilt angle is 90 degrees different than the desired phi parameter, which can thus be determined using a 1-dimensional search, constructing the field measurements along the second line of zeros, and determining the tilt angle that minimizes the total field energy in the candidate direction. This provides the phi estimate.
Finally, the distance along the line from the x-y plane intersection of first line of zeros and the plane of zeros, to the dipole magnet center is determined based on a 1-dimensional search that searches for the best agreement between the measured fields and the predicted fields along this line. In an example, the minimum value of a convergence metric along this line will correspond to the x-y-z dipole magnet center.

Feature extraction and table lookup method. It is noted that whatever pattern is generated in the magnetic fields will be rotated and translated with whatever rotation and translation is performed on the dipole magnet for translation in x and y and rotation in theta. This means that if there are features that can be extracted in a system constrained to a particular set of x, y and theta, they can be mapped to a different arbitrary set of x, y, and theta, such as x=0, y=0, theta=0 (for convenience of calculation). This leaves only 2 values undefined: phi (elevation) and z (height above the sensor grid).

If the rotatable and translatable constraint at x=0, y=0, and theta=0 is maintained, metrics can be defined as being constructed as a function of the magnetic field measurements, phi and z. There are many different metrics that can be constructed from these inputs, but the goal here is to define a set of metrics such that over the full range of phi and z inputs, there is a useful mapping back from the calculated metrics to an estimate for the phi and z pair. It is noted that a single metric may not provide a good one-to-one mapping back to the phi/z pair over the entire range of the search, so it may be advantageous to use different metrics over different combined ranges for the phi/z pair.

In an example, the phi/z pair may be characterized using one or more of the following functions: pos_peakx, neg_peakx, pos_neg_ratio, peak_sep, 2Dmag_peak, and 3Dmag_peak.

In some embodiments, and given the calculated metrics, the optimal phi/z pair can be determined by searching along z. In an example, this includes
 (a) selecting a candidate value for z;
 (b) given the calculated metrics, use the table to perform an interpolated lookup of the best phi value corresponding to the metric set and the z candidate;
 (c) calculate the convergence error between the predicted field measurements that would result from this combination of phi/z and the actual measurements; and
 (d) determine the best value for z by following the gradient of the convergence error toward its minimum. This gives us the estimates for phi and z.

The aforementioned description results in estimates for phi, theta and z, and an equation for a line containing x and y. Given that the metric/table model can be rotated in theta and translated in x and y, the distance along the identified first line of zeros relative to the table origin can be calculated. The field metric tables provide multiple estimates of this remaining offset. For example, the pos_peakx value is the distance along the first line of zeros in the x-y plane between the dipole magnet's geometric center and the location of the field peak value along the direction defined by the first line of zeros. Thus, x and y values can be estimated by starting with the x-y position of the peak of the 2D field magnitude (in x and y), then moving in the direction of the first line of zeros by an amount equal to pos_peakx.

In some embodiments, the geometric feature extraction method can be used to derive the five parameters. In other embodiments, the feature extraction and table lookup method can be used to derive the five parameters. In yet other embodiments, both methods are used and the individual x, y, z, theta and phi parameter estimates are blended by performing a weighted average of the convergence errors of each method.

In an example, a convergence error is defined as follows: for each measured sensor location, there exists a measured magnetic field value for x, y and z. For a given set of model parameters, the predicted magnetic field values for x, y and z at the same set of sensor locations can be calculated. Then, calculating the sum of $(xmeas-xpred)^2$, $(ymeas-ypred)^2$, and $(zmeas-zpred)^2$ across all locations provides an error metric for the first geometric feature extraction method and a second error metric for the second table-lookup method. For each of the 5 parameters, the blended parameter estimate will be Param_method1*(error_sum2/(error_sum1+error_sum2))+Param_method2*(error_sum1/(error_sum1+error_sum2)).

Refinement process. The goal of the above two methods is to provide a set of parameter estimates that are close enough to the true (real) values such that the closest local minimum of a defined convergence metric is in fact the global minimum. In some embodiments, a refinement stage (illustrated in FIG. 15) is an N-dimensional partial derivative driven convergence method, whose implementation includes scaled ranges, initialization, and auto-calibration. The initialization procedure for the refinement process includes:
 (a) setting initial conditions for candidate parameter values. In an example, these can be from an intermediate optimizer. In another example, they can be generated by a geometric estimator. In yet another example, they can be default values;
 (b) calculating predicted field measurements at sensor locations given initial parameter values;
 (c) calculating a starting convergence metric based on differences between measured field values at sensors and predicted sensor values;
 (d) setting a list of relative scale factors for the model parameters. In an example, the scale factors should be set so that the ratio of update gain to total expected parameter range is about the same for all parameters. In some embodiments, if the scaling is mismatched, the refinement process operates sub-optimally;
 (e) setting a second global gain factor. In an example, the variable global gain factor and the constant per parameter initial scale factors will be used as a combined scale factor for correction gain after calculating the set of partial derivatives of the convergence metric relative to each parameter. The set of partial derivatives is normalized to have the sum of squares of scaled partial derivatives scaled to one;
 (f) calculating a new set of candidate parameter values and convergence metric;
 (g) accepting the new candidate parameter values if the convergence metric for the new candidate is better than the prior best (allowing for slight increase in the global scale factor);
 (h) rejecting the new candidate parameter values if the convergence metric for the new candidate is not an improvement, and reducing the overall variable system gain based on the assumption that the current step sizes are too large. In an example, the gain is divided by two;
 (i) completing the process if the system gain has decreased below a minimum threshold or if a maximum number of iterations have been exceeded; and
 (j) outputting the best parameter values and final convergence metric.

In operation (h) of the above process, it is noted that the system gain is not reduced, and it may be increased slightly to improve convergence of the algorithm.

The refinement technique described above will work for any number of dimensions so long as the convergence metric local minimum function of N dimensions is also the global minimum. Thus, the refinement stage can be extended to perform an auto-calibration procedure on geometric parameters that may not be perfectly known, such as the pole separation distance of the dipole magnet and the absolute strength of the dipole.

In an example, if a good (but not exact) estimate of pole strength and separation distance is available, they could be included directly in the same optimization used to find values for the other parameters. However, if good estimates do not exist, then it is preferable to first perform the 5D optimization on x, y, z, theta and phi, and once these have converged to a minimum value using the assumed values for pole separation and magnetic field strength, add these last two parameters to the optimization model (now 7D) and re-optimize.

Multiple-magnet system. In some embodiments, computing approximate model parameters for a two-magnet system includes operations similar to those for the single-magnet systems. Some geometric features can be extracted by treating the magnets separately, while others require different methods. Some examples of geometric features that can be computed in the multiple-magnet system include, but are not limited to, the following:

(a) Magnitude peak estimates for x-y projection of magnet coordinates

The maximum magnitudes of the total magnetic field occur near the sensor grid points that are closest to the magnets. For z parameters that are small compared to the grid spacing, there are two distinct peaks per magnet: one near each pole. As z increases, the individual poles are no longer resolvable from the magnitude, and there is only one peak per magnet.

For each magnet, the x and y location of the magnitude peak approximates the projection of the center point onto the x-y plane. These estimates have errors caused by the other magnet and by the spacing of the measurements. As the magnets' z increase, the errors increase as the influence of the other magnet grows.

Since the sensor grid spacing has a similar scale to the dimensions of the magnets themselves, some embodiments are configured to improve the precision of the estimated peak locations. In an example, polynomial interpolation can be used to approximate intermediate values between the measurements at the sensor locations. An upsampling factor L is selected and a finer grid of points is computed by fitting a polynomial function to the existing data points. For well-behaved functions such as the magnetic field strength, the approximation can be quite close to the correct values. This technique can mitigate some of the effects of the coarseness of the sensor grid. It is important to note that interpolation is most useful close to a pole, where magnitude changes are larger and not complicated by other influences.

(b) Peak total field magnitude estimates for magnet z coordinate

Figure 22:
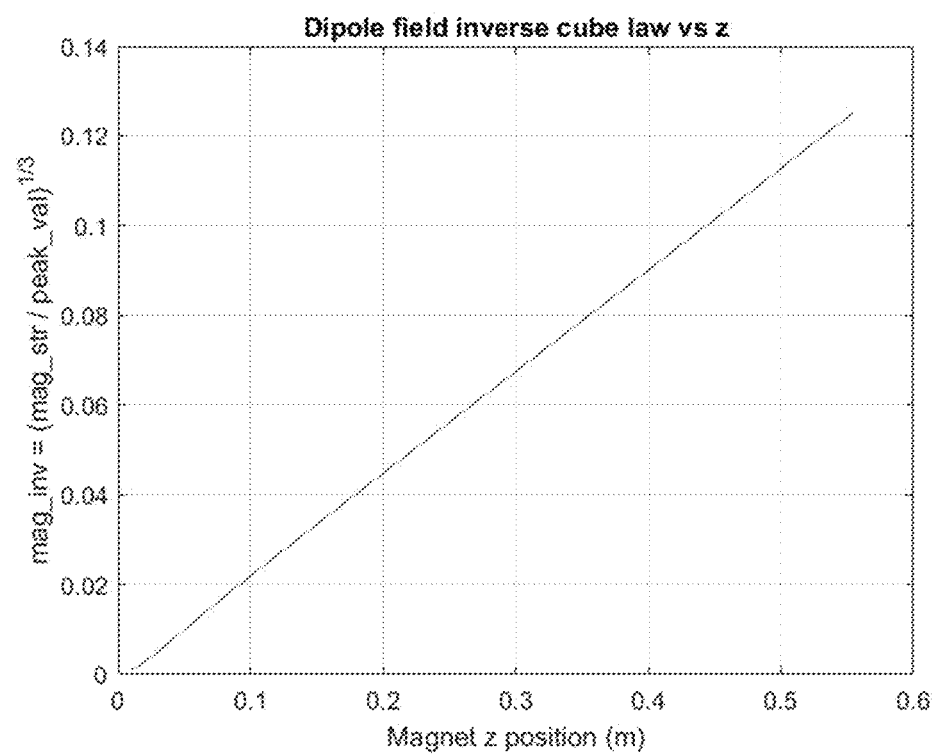
FIG. 22 illustrates an example of the dipole inverse cube law.

When the distance to the dipole magnet is much greater than the pole separation distance, the dipole's field magnitude varies with the distance r as $1/r^3$ as r increases (as illustrated in the example in FIG. 22).

Figure 21:
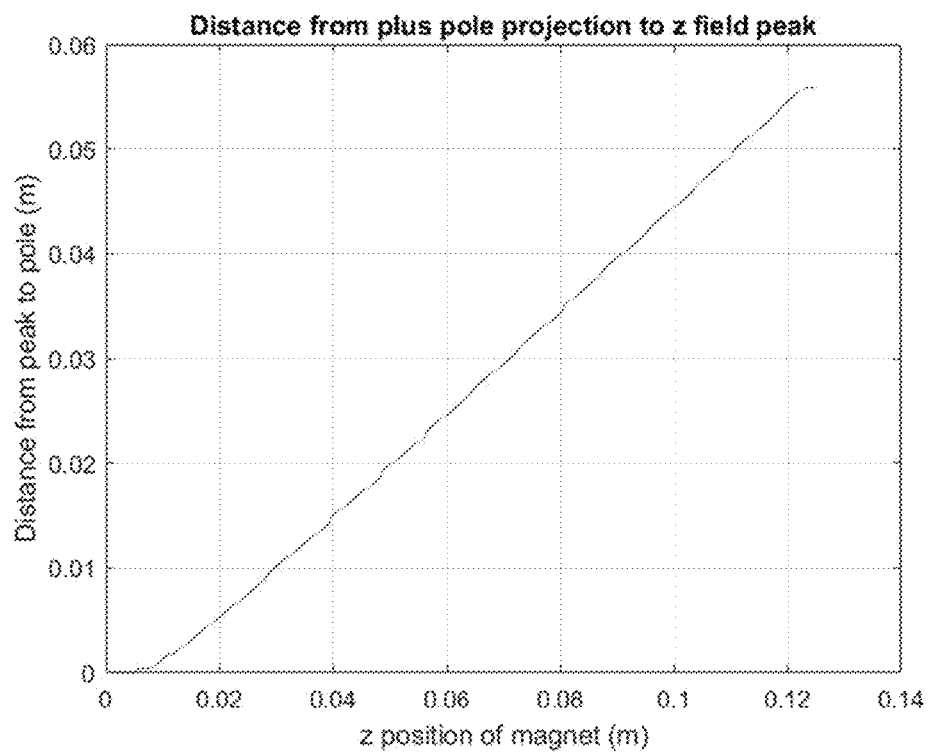
FIG. 21 illustrates an example of the distance between the positive pole projection to the z-field peak in a two magnet system.

For measurements taken much closer to the dipole magnet, if the distance to one pole is significantly less than the pole separation distance, the near pole dominates and the field drops off as approximately $1/r^2$. In the transition region between the far-field and the near-field, the power-relationship is in-between the two bounding cases. Inverting this relationship allows the distance to be estimated from the field strength at the peak coordinates. Since the peak is close to the magnet center's projection, this distance is an estimate of the z parameter (as illustrated in the example in FIG. 21).

At each sensor location, the z component of the magnetic field has contributions from the four magnetic poles. The closer a sensor is to one of the poles, the stronger the influence of that pole, and the smaller are the errors due to neglecting the others.

(c) Magnetic field z component estimates for theta angles for each magnet

Figure 23:
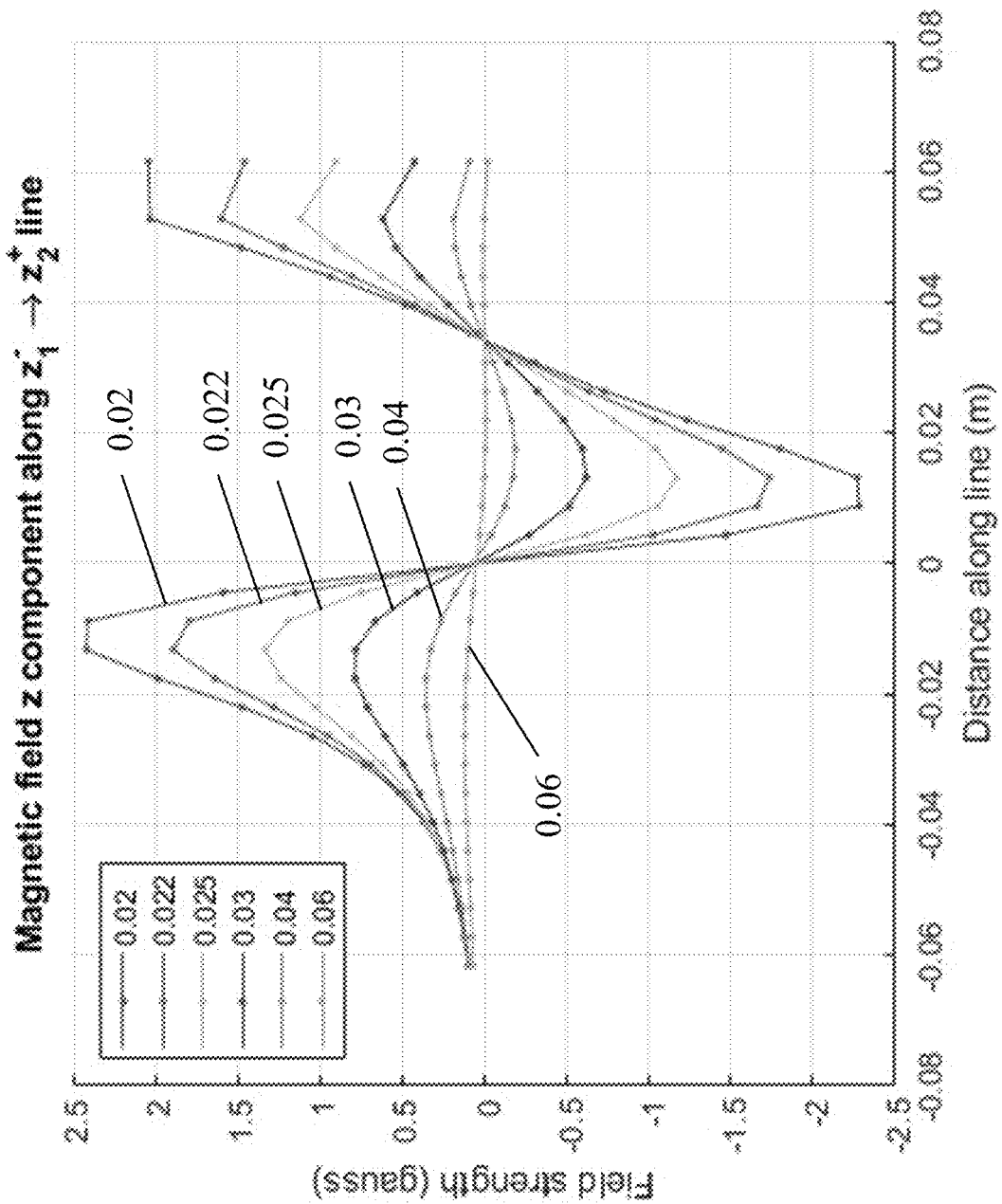
FIG. 23 illustrates an example of the curve family of the z-field component along the line from $z_1^-$ to $z_1^+$ for varying z.

Maxima of the z field components, denoted by $z_1^+$ and $z_2^+$, approximate the x-y plane projections of the magnets' plus (or north) poles when z is small compared to the pole spacing. Conversely, the minima of the z field are denoted by $z_1^-$ and $z_2^-$ and approximate the minus (or south) poles when the magnet is close to the plane. The extrema move progressively farther apart as z is increased, so their locations cannot be used as a direct estimate of the location without compensating for z. In principle however, the line between a magnet's z plus and z minus peaks lies along the projection of the magnet's axis and can be used directly to estimate the theta parameter. FIG. 23 illustrates an example of the curve family of the z-field component along the line from $z_1^-$ to $z_1^+$ for varying z.

Significant discrepancies in the z field peaks of each magnet are caused by the influence of the other magnet. As the z field is just one component rather than the total magnitude, effects that tend to rotate the field vector contribute directly to errors in a single component. These discrepancies are greatest for the center two poles, that is, for $z_1^-$ and $z_2^+$, which are substantially affected by all the other poles. Since the peaks due to these poles tend to get closer together as z increases, they become indistinguishable from each other for larger values of z. The peaks due to the outside poles $z_1^+$ and $z_2^-$ how much greater amplitudes and are much more easily discernable due to their greater distance from the other magnets.

Instead of trying to distinguish separate peaks for the two center poles, the direction of fastest change away from the outside peaks is used to estimate the line along which the corresponding inside peak would lie. Values of the directional derivative (defined as the dot product of a unit vector with the gradient) are computed for points in a circle pointing away from the outside peak. Close to this pole, the z field changes most along the projection of the magnet's axis before other poles start influencing the field. This direction of greatest ascent gives a direct estimate of the angle between the magnet's z peaks.

To determine the distance from the outside pole to its corresponding center pole, the point along the line of greatest ascent (or descent) is found where the first difference of the gradient magnitude is a minimum. This is a characteristic of an inflection point, a point at which the rate of change is constant. For the case of an opposite charge tending to cancel out the center pole, this is the farthest point before the other magnet starts exerting equivalent influence over the field. The distance along the gradient line provides an estimate of the center pole's location.

(d) Associate magnitude peaks with their corresponding z plus and z minus peaks

May be used as an independent calculation to improve robustness.

When multiple maxima and minima are found for total magnitude and z field component, these points are grouped into a triplet that represents one magnet. Naïve approaches such as taking the closest peaks can fail for the two center poles for larger values of the alpha parameter.

Create an exhaustive list of the possible groups of every magnitude peak with a z plus and a z minus peak. For each possible association of every magnitude peak with a z plus and a z minus, compute the sum of the distances from the magnitude peak to z component peaks. Select the grouping with the smallest total sum.

(e) Distinguish magnet 1 peak groups from magnet 2 peak groups

The arrangement of the magnets with magnet 1's plus pole at the edge, magnet 1's minus pole and magnet 2's plus pole in the center, then magnet 2's minus pole at the other edge allows the two magnets to be distinguished.

For an arbitrary selection of z1 and z2, compute vectors from z1_plus→z1_minus→z2_plus and z2_plus→z2_minus→z1_plus. Because the alpha parameter ranges from −90 to 90 degrees, only the z2-to-z1 vector will point in the opposite direction from its plus-to-minus vector.

Find the angle between these pairs of vectors and compare them. If M1 and M2 have been chosen correctly, the z1→z2 angle will be greater than the z2→z1 angle. If this relation does not hold, the magnets have been switched.

In some embodiments, computations can be implemented for a parameterized curve for the flexible guidewire section. Herein, it must be noted that although curve families that can be traced by a flexible interconnect section between two magnets can be precisely characterized, small errors in the curve family equations translate to overall position errors. However, if the curve family is fairly close, the 7D optimization can be performed to be close enough so that the 7-parameter system estimate can be converted into a 10-parameter model estimate, which is followed by a final 10D refinement stage (e.g., in the context of FIGS. 14 and 15). This approach may be used for two or more magnets, and includes picking a curve shape for the flexible guidewire section, e.g., a section of an arc corresponding to a constant curvature along the flexible section, and perform a 7D parameter estimation for the extremal points. In an example, this approach is characterized by:

(a) the alpha deflection angle mapping to an ellipse rather than a single hinge deflection;
(b) the predicted signal using three or more magnets in the model, and x, y, and z being calculated for each of the 6 magnetic poles from the 7-parameter model; and
(c) the 7D model providing a fairly good estimate (if, for example, the assumed curve shape of the wire is not a perfect match for the actual wire shape), and a 15D optimization being able to converge to the correct values.

In some embodiments, the computations may be performed with two thresholds: a low threshold and a high threshold. If convergence metric is greater than the high threshold, then the final refinement is performed. If, however, the convergence metric does not exceed the high threshold but is greater than the low threshold, the intermediate refinement may be performed.

According to some embodiments of the disclosed technology, a three-stage approach to generate position and orientation estimates for an N-magnet system with an approximate rotational compliance model comprises:

(a) an initial geometric feature extraction;
(b) a 7-parameter model extraction (also referred to as an intermediate refinement, which can be exact in some cases, but approximate in the general case, but much more accurate than the initial geometric feature extraction); and
(c) a 5D×N partial derivative refinement, with N permanent magnets with some bounding constraints on the relative orientations of the N magnets.

In some embodiments, there will be non-zero errors in the physical dimensions of the guidewire, the mounting locations and orientations of the permanent magnets relative to each other, the magnet lengths and their field strengths. If uncorrected, these will contribute error to the overall location estimate. In this case, the model parameter refinement stage can be extended to perform auto-calibration of these mounting, size and strength errors. Each parameter in need of per guidewire calibration is included in the partial derivative convergence metric.

In an example, assume that there are two cylindrical magnets of lengths D1 and D2 and field strengths S1 and S2, and that the guidewire is two rigid sections with a single hinge between the two permanent magnets. The calibration of D1, D2, S1 and S2 is performed by using an 11-parameter partial derivative optimizer with the parameters: [x1 y1 z1 theta1 phi1, alpha (deflection angle of the hinge), eta (rotation about the first cylindrical magnet axis), D1, D2, S1 and S2].

In some embodiments, the in-body localization approaches described in this document can be applied to endoscopic, broncho-scopic, cardio- and neuro-applications, using one or more permanent magnets incorporated into the medical device.

Figure 24:
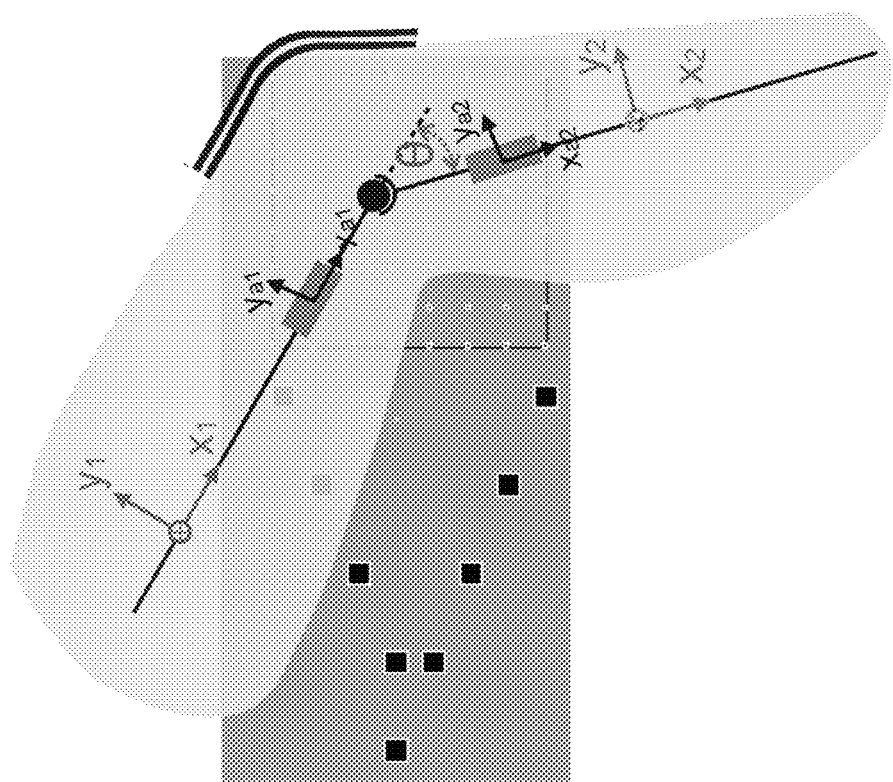
FIG. 24 illustrates an example of a two magnet physical therapy system with magnets mounted across flexible knee joint.

In some embodiments, the disclosed technology can be applied to physical therapy applications (as illustrated in FIG. 24). As illustrated therein, two fixed magnets can be mounted on either side of the knee joint to analyze joint flexure. In an example, the magnets may be incorporated into an adhesive mount. In another example, the sensor grid array can be oriented in any manner, e.g., flag on the ground or next to joint flexure in vertical sheet.

Figure 25:
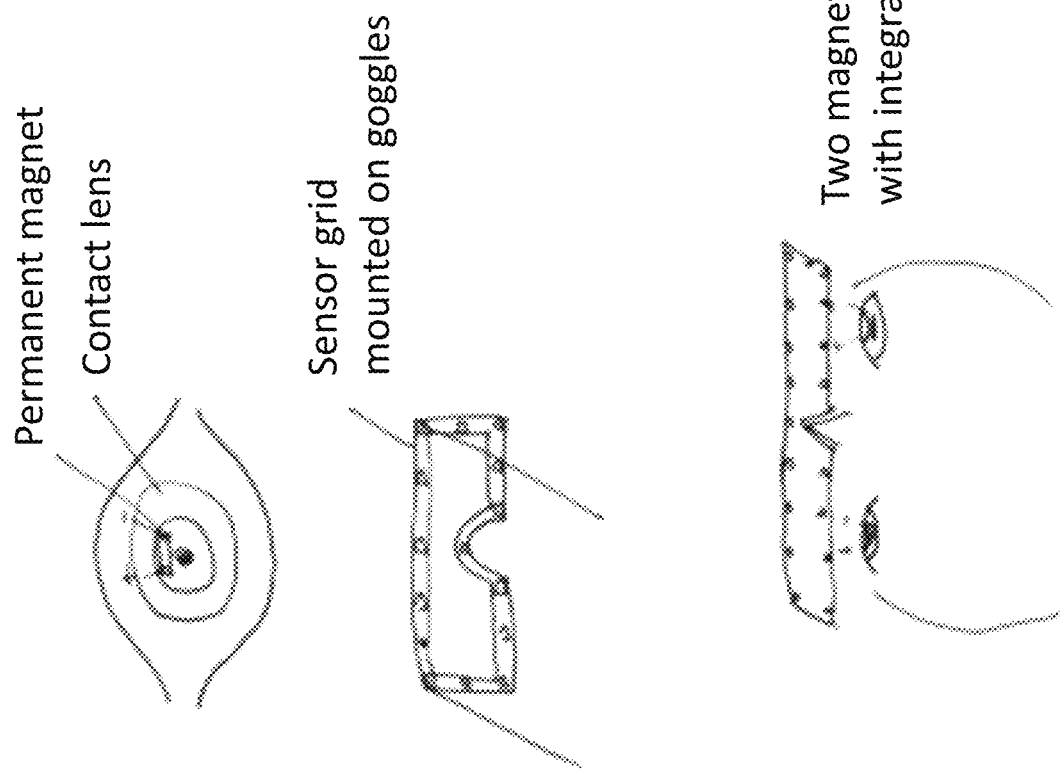
FIG. 25 illustrates an example of an eye tracking system with contact lens-mounted permanent magnets and goggles-mounted sensor array.

In some embodiments, head tracking and eye tracking applications can be supported based on the disclosed technology. An example eye-tracking system is illustrated in FIG. 25. As illustrated therein, a single permanent magnet can be affixed to a contact lens with the grid sensor array being incorporated into the glasses, goggles or helmet.

Figure 26:
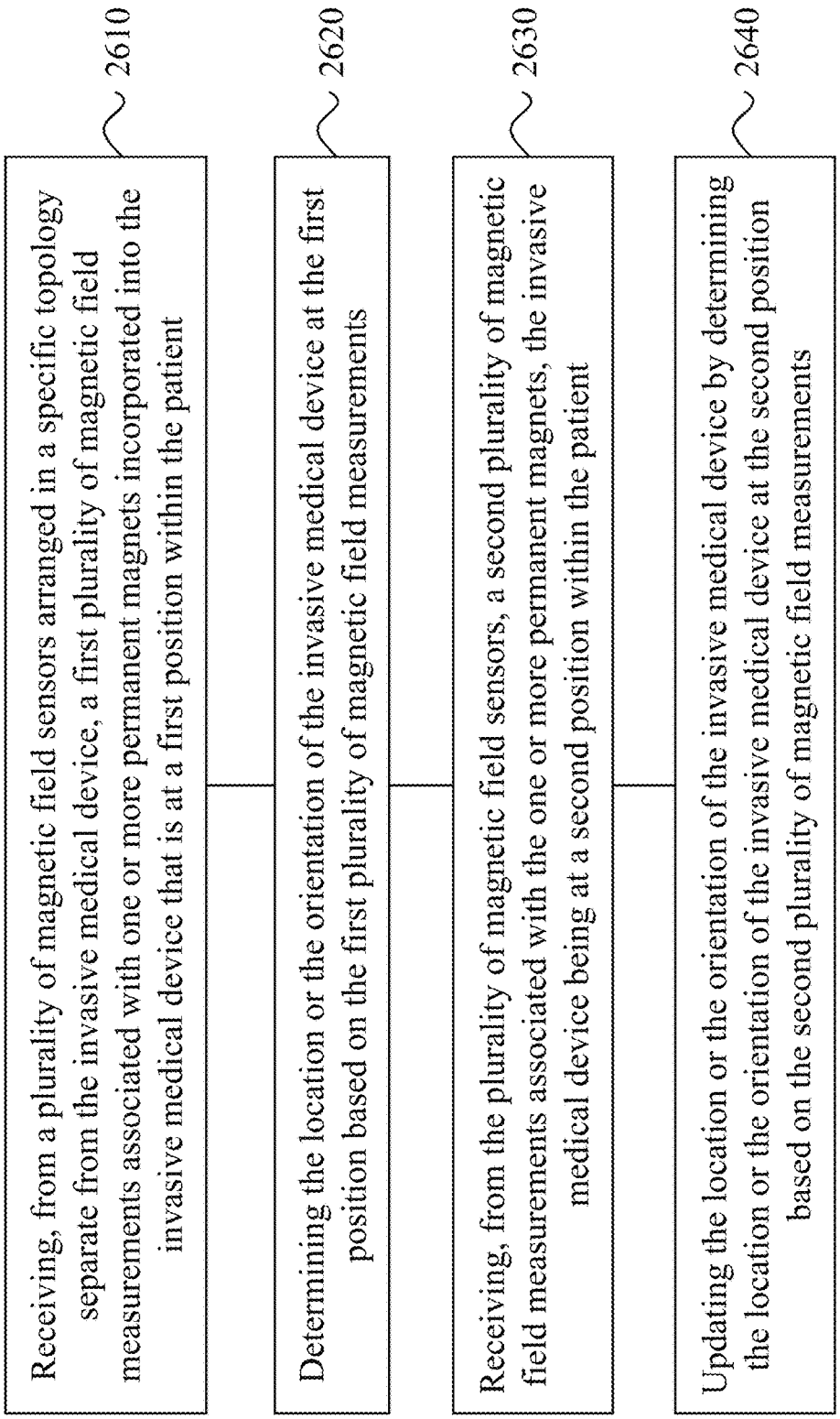
FIG. 26 is a flowchart of an example method for location and orientation of a medical device incorporating one or more permanent magnets.

FIG. 26 illustrates a flowchart of an example method 2600 for estimating the position and orientation of an invasive medical device within a patient. The method 2600 includes, at operation 2610, receiving, from a plurality of magnetic field sensors arranged in a specific topology separate from the invasive medical device, a first plurality of magnetic field measurements associated with one or more permanent magnets incorporated into the invasive medical device that is at a first position within the patient.

The method 2600 includes, at operation 2620, determining the location or the orientation of the invasive medical device at the first position based on the first plurality of magnetic field measurements.

The method 2600 includes, at operation 2630, receiving, from the plurality of magnetic field sensors, a second plurality of magnetic field measurements associated with the one or more permanent magnets, the invasive medical device being at a second position within the patient.

The method 2600 includes, at operation 2640, updating the location or the orientation of the invasive medical device by determining the location or the orientation of the invasive medical device at the second position based on the second plurality of magnetic field measurements.

In some embodiments, the one or more permanent magnets consists of a single magnet, and the operation of determining the location or the orientation of the invasive medical device at the first position, in method 2600, comprises generating, based on the first plurality of magnetic field measurements, an initial estimate for each of a plurality of parameters of a model for the location and the orientation of the invasive medical device, and performing, based on the first plurality of magnetic field measurements and the initial estimate for each of the plurality of parameters, a refinement calculation to generate a final estimate for each of the plurality of parameters.

In some embodiments, the model for the location and the orientation of the invasive medical device comprises five parameters or seven parameters.

In some embodiments, the one or more permanent magnets comprises N permanent magnets, and N is a positive integer.

In some embodiments, the refinement calculation comprises a 5×N-dimensional iterative partial derivative-based optimization.

In some embodiments, the method 2600 further includes the operation of updating the model based the final estimate for each of the plurality of parameters.

In some embodiments, the invasive medical device is a catheter, a catheter guidewire, or a self-guided electrophysiology (EP) catheter.

Embodiments of the disclosed technology further provide a system for estimating a location or an orientation of an invasive medical device that includes one or more permanent magnets incorporated into the invasive medical device, a plurality of magnetic field sensors arranged in a specific topology separate from the invasive medical device, the plurality of magnetic field sensors configured to obtain a plurality of magnetic field measurements of the one or more permanent magnets of the invasive medical device, and one or more processors, coupled to the plurality of magnetic field sensors, configured to receive the plurality of magnetic field measurements, and enable a calculation of the location or the orientation of the one or more permanent magnets based on the plurality of magnetic field measurements.

In some embodiments, the one or more processors are configured, as part of enabling the calculation of the location or the orientation of the one or more permanent magnets, to obtain, based on the plurality of magnetic field measurements, a plurality of differing magnetic field strength values associated with at least a subset of the magnetic field sensors, and determine the location or the orientation of the one or more permanent magnets using the plurality of differing magnetic field strength values.

In some embodiments, the invasive surgical device comprises a catheter or a self-guided electrophysiology (EP) catheter.

In some embodiments, the one or more permanent magnets consists of a single permanent magnet at a distal end of the invasive medical device.

In some embodiments, the one or more permanent magnets comprises a first permanent magnet at a distal end of the invasive medical device and a second permanent magnet that is separated from the first permanent magnet by a non-magnetic portion of the invasive medical device.

In some embodiments, the non-magnetic portion comprises (a) a flexible portion, (b) two rigid portions with a hinge between the two rigid portions, or (c) a flexible circular arc with a predetermined radius.

In some embodiments, the one or more permanent magnets comprises three magnets with a first flexible portion between a first magnet at a distal end of the invasive medical device and a second magnet, and a second flexible portion between the second magnet and the third magnet.

In some embodiments, the invasive medical device is a catheter guidewire.

In some embodiments, each of the one or more permanent magnets comprises a stainless steel mesh integrated with the invasive medical device.

In some embodiments, the specific topology is a uniformly-spaced planar grid.

In some embodiments, the invasive medical device is located within a perimeter of the uniformly-spaced planar grid.

In some embodiments, a spacing between two adjacent magnetic field sensors is substantially similar to a dimension of the one or more permanent magnets.

In some embodiments, the specific topology is a planar grid with irregular separations between adjacent magnetic field sensors.

In some embodiments, the specific topology comprises positioning of the plurality of magnetic field sensors in three dimensions.

In some embodiments, the plurality of magnetic field sensors is configured as a set of stationary sensors positioned outside of a patient's body when the invasive medical device is inserted into a cavity or an orifice of the patient's body.

In some embodiments, the one or more processors is further configured, as part of enabling the calculation of the location or the orientation of the one or more permanent magnets, to perform, based on the plurality of magnetic field measurements, a geometric feature extraction calculation to generate an initial estimate for each of a plurality of parameters of a model for the location and the orientation of the invasive medical device, and perform, based on the plurality of magnetic field measurements and the initial estimate for each of the plurality of parameters, a refinement calculation to generate a convergence metric and a final estimate for each of the plurality of parameters.

In some embodiments, the one or more processors is further configured to update the model based the final estimate for each of the plurality of parameters.

It is understood that the various disclosed embodiments may be implemented individually, or collectively, in devices comprised of various components, electronics hardware and/or software modules and components. These devices, for example, may comprise a processor, a memory unit, an interface that are communicatively connected to each other, and may range from desktop and/or laptop computers, to mobile devices and the like. The processor and/or controller can perform various disclosed operations based on execution of program code that is stored on a storage medium. The processor and/or controller can, for example, be in communication with at least one memory and with at least one communication unit that enables the exchange of data and information, directly or indirectly, through the communication link with other entities, devices and networks. The communication unit may provide wired and/or wireless communication capabilities in accordance with one or more communication protocols, and therefore it may comprise the proper transmitter/receiver antennas, circuitry and ports, as well as the encoding/decoding capabilities that may be necessary for proper transmission and/or reception of data and other information.

Implementations of the subject matter and the functional operations described in this patent document can be implemented in various systems, digital electronic circuitry, or in computer software, firmware, or hardware, including the structures disclosed in this specification and their structural equivalents, or in combinations of one or more of them. Implementations of the subject matter described in this specification can be implemented as one or more computer program products, i.e., one or more modules of computer program instructions encoded on a tangible and non-transitory computer readable medium for execution by, or to control the operation of, data processing apparatus. The computer readable medium can be a machine-readable storage device, a machine-readable storage substrate, a memory device, a composition of matter effecting a machine-readable propagated signal, or a combination of one or more of them. The term "data processing unit" or "data processing apparatus" encompasses all apparatus, devices, and machines for processing data, including by way of example a programmable processor, a computer, or multiple processors or computers. The apparatus can include, in addition to hardware, code that creates an execution environment for the computer program in question, e.g., code that constitutes processor firmware, a protocol stack, a database management system, an operating system, or a combination of one or more of them.

A computer program (also known as a program, software, software application, script, or code) can be written in any form of programming language, including compiled or interpreted languages, and it can be deployed in any form, including as a stand-alone program or as a module, component, subroutine, or other unit suitable for use in a computing environment. A computer program does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform functions by operating on input data and generating output. The processes and logic flows can also be performed by, and apparatus can also be implemented as, special purpose logic circuitry, e.g., an FPGA (field programmable gate array) or an ASIC (application specific integrated circuit).

Processors suitable for the execution of a computer program include, by way of example, both general and special purpose microprocessors, and any one or more processors of any kind of digital computer. Generally, a processor will receive instructions and data from a read only memory or a random access memory or both. The essential elements of a computer are a processor for performing instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. However, a computer need not have such devices. Computer readable media suitable for storing computer program instructions and data include all forms of nonvolatile memory, media and memory devices, including by way of example semiconductor memory devices, e.g., EPROM, EEPROM, and flash memory devices. The processor and the memory can be supplemented by, or incorporated in, special purpose logic circuitry.

While this patent document contains many specifics, these should not be construed as limitations on the scope of any invention or of what may be claimed, but rather as descriptions of features that may be specific to particular embodiments of particular inventions. Certain features that are described in this patent document in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. Moreover, the separation of various system components in the embodiments described in this patent document should not be understood as requiring such separation in all embodiments.

Only a few implementations and examples are described and other implementations, enhancements and variations can be made based on what is described and illustrated in this patent document.

What is claimed is:

1. A method for obtaining a location or an orientation of an invasive medical device inside a patient, comprising:
   receiving, from a plurality of magnetic field sensors arranged in a specific topology separate from the invasive medical device, a first plurality of magnetic field measurements associated with one or more permanent magnets incorporated into the invasive medical device that is at a first position within the patient, wherein the one or more permanent magnets is at a height above the specific topology that is less than or equal to twice a width of the specific topology;
   determining the location or the orientation of the invasive medical device at the first position based on the first plurality of magnetic field measurements,
   wherein the determining the location or the orientation comprises:
      performing, based on the first plurality of magnetic field measurements, a geometric feature extraction calculation to generate an initial estimate for each of a plurality of parameters of a model for the location and the orientation of the invasive medical device, and performing, based on the first plurality of magnetic field measurements and the initial estimate for each of the plurality of parameters, a refinement calculation to generate a convergence metric and a final estimate for each of the plurality of parameters, wherein the refinement calculation comprises an N-dimensional partial derivative driven convergence method, wherein a predicted value of at least one of the first plurality of magnetic field measurements converges to a corresponding one of the first plurality of magnetic field measurements, and wherein N is a positive integer;

receiving, from the plurality of magnetic field sensors, a second plurality of magnetic field measurements associated with the one or more permanent magnets, wherein the invasive medical device is at a second position within the patient; and updating the location or the orientation of the invasive medical device by determining the location or the orientation of the invasive medical device at the second position based on the second plurality of magnetic field measurements.

2. The method of claim 1, wherein the model for the location and the orientation of the invasive medical device comprises five parameters or seven parameters.

3. The method of claim 1, wherein the one or more permanent magnets comprises N permanent magnets.

4. The method of claim 3, wherein the refinement calculation comprises a 5×N-dimensional iterative partial derivative-based optimization.

5. The method of claim 1, further comprising:
updating the model based the final estimate for each of the plurality of parameters.

6. The method of claim 1, wherein the invasive medical device is a catheter or a self-guided electrophysiology (EP) catheter.

7. The method of claim 6, wherein the one or more permanent magnets consists of a single permanent magnet at a distal end of the invasive medical device.

8. The method of claim 6, wherein the one or more permanent magnets comprises a first permanent magnet at a distal end of the invasive medical device and a second permanent magnet that is separated from the first permanent magnet by a non-magnetic portion of the invasive medical device.

9. The method of claim 8, wherein the non-magnetic portion comprises (a) a flexible portion, (b) two rigid portions with a hinge between the two rigid portions, or (c) a flexible circular arc with a predetermined radius.

10. The method of claim 6, wherein the one or more permanent magnets comprises three magnets with a first flexible portion between a first magnet at a distal end of the invasive medical device and a second magnet, and a second flexible portion between the second magnet and a third magnet.

11. The method of claim 1, wherein the invasive medical device is a catheter guidewire.

12. The method of claim 11, wherein each of the one or more permanent magnets comprises a stainless steel mesh integrated with the invasive medical device.

13. The method of claim 11, wherein the one or more permanent magnets comprises at least one cylindrical magnet surrounding one or more central lumens of the catheter guidewire.

14. The method of claim 1, wherein the specific topology is a uniformly-spaced planar grid.

15. The method of claim 14, wherein the invasive medical device is located within a perimeter of the uniformly-spaced planar grid.

16. The method of claim 14, wherein a spacing between two adjacent magnetic field sensors is similar to a dimension of the one or more permanent magnets.

17. The method of claim 1, wherein the specific topology is a planar grid with irregular separations between adjacent magnetic field sensors.

18. The method of claim 1, wherein the specific topology comprises positioning of the plurality of magnetic field sensors in three dimensions.

19. The method of claim 1, wherein the plurality of magnetic field sensors is configured as a set of stationary sensors positioned outside of the patient.

20. A non-transitory computer-readable storage medium having instructions stored thereupon that are executable by a processor for obtaining a location or an orientation of an invasive medical device inside a patient, comprising:

instructions for receiving, from a plurality of magnetic field sensors arranged in a specific topology separate from the invasive medical device, a first plurality of magnetic field measurements associated with one or more permanent magnets incorporated into the invasive medical device that is at a first position within the patient, wherein the one or more permanent magnets is at a height above the specific topology that is less than or equal to twice a width of the specific topology;

instructions for determining the location or the orientation of the invasive medical device at the first position based on the first plurality of magnetic field measurements, wherein the instructions for determining the location or the orientation comprises:

instructions for performing, based on the first plurality of magnetic field measurements, a geometric feature extraction calculation to generate an initial estimate for each of a plurality of parameters of a model for the location and the orientation of the invasive medical device, and instructions for performing, based on the first plurality of magnetic field measurements and the initial estimate for each of the plurality of parameters, a refinement calculation to generate a convergence metric and a final estimate for each of the plurality of parameters, wherein the refinement calculation comprises an N-dimensional partial derivative driven convergence method, wherein a predicted value of at least one of the first plurality of magnetic field measurements converges to a corresponding one of the first plurality of magnetic field measurements, and wherein N is a positive integer;

instructions for receiving, from the plurality of magnetic field sensors, a second plurality of magnetic field measurements associated with the one or more permanent magnets, wherein the invasive medical device is at a second position within the patient; and instructions for updating the location or the orientation of the invasive medical device by determining the location or the orientation of the invasive medical device at the second position based on the second plurality of magnetic field measurements.

* * * * *